United States Patent [19]
Parker et al.

[11] Patent Number: 5,945,576
[45] Date of Patent: Aug. 31, 1999

[54] MOUSE MODEL OF PSORIASIS

[75] Inventors: Christina M. Parker, Newton Centre; Michael P. Schön, Boston, both of Mass.

[73] Assignee: Brigham & Women's Hospital, Inc., Boston, Mass.

[21] Appl. No.: 08/628,761

[22] Filed: Apr. 5, 1996

[51] Int. Cl.$^6$ .............................. C12N 5/00; C12N 15/00; A01N 63/00; A61K 49/00
[52] U.S. Cl. .............................. 800/9; 435/375; 435/377; 424/93.7; 424/9.21
[58] Field of Search .................................. 435/375, 377; 800/2, DIG. 5, DIG. 4, 9; 424/93.7, 9.21

[56] References Cited

U.S. PATENT DOCUMENTS 5,368,854  11/1994  Rennick ................................. 424/85.2

FOREIGN PATENT DOCUMENTS

WO 90/15869  12/1990  WIPO ............................. C12N 15/00
WO 94/23760  10/1994  WIPO ............................. A61K 67/00

OTHER PUBLICATIONS

Wrone–Smith et al. "Dermal injection of immunocytes induces psoriasis" Journal of Clinical Investigation, vol. 98, No. 8, pp. 1878–1887 (1996).

Petzelbauer et al "Human delayed–type hypersensitivity reaction in a SCID mouse engrafted with human T cells and autologous skin" The Journal of Investigative Dermatology, vol. 107, No. 4, pp. 577–581 (1996).

Powrie et al. "Phenotypically distinct subsets of CD4 + T cells induce or protect from chronic intestinal inflammation in C. B–17 scid mice" Int'l Immuno. vol. 5, No. 11, pp. 1461–1471 (1993).

Nickoloff et al. "Severe combined immunodeficiency mouse and human psoriatic skin chimeras" American Journal of Pathology vol. 146, No. 3, pp. 580–588 (1995).

Fiona Powrie et al., "Regulatory Interactions between CD45RB$^{high}$ and CD45RB$^{low}$ CD4$^+$ T Cells Are Important for the Balance between Protective and Pathogenic Cell-–mediated Immunity", J. Exp. Med. Feb. 1994, pp. 589–600, The Rockefeller University Press, vol. 179.

F. Powrie et al., "Transfer of CD4 $^+$ T cells to C.B–17 SCID mice: a model to study Th1 and Th2 cell differentiation and regulation in vivo", Research in Immunology 145(5): 347–353 (1994).

Fiona Powrie et al., "Inhibition of Th1 Responses Prevents Inflammatory Bowel Disease in scid Mice Reconstituted with CD45RB$^{h1}$ CD4$^+$ T Cells", Oct. 1994, pp. 553–562, Immunity, vol. 1.

Fiona Powrie et al., "Phenotypically distinct subsets of CD4$^+$ cells induce or protect from chronic intestinal inflammation in C. B–17 scid mice", Jun. 1993, pp. 1461–1471, International Immunology, vol. 5, No. 11.

P.J. Morrissey et al., "Induction of wasting disease in SCID mice by the transfer of normal CD$^+$/CD45RB$^{h1}$ T cells and the regulation of the autoreactivity by CD4 $^+$/CD45RB$^{low}$", Research in Immunology, 145(5):357–362 (1994).

Tracey J. Smith et al., "Murine M290 Integrin Expression Modulated by Mast Cell Activation", Aug. 1994, pp. 393–403, Immunity, vol. 1.

Joel D. Taurog, et al., "Susceptibility to Inflammatory Disease in HLA–B27 Transgenic Rat Lines Correlates with the Level of B27 Expression$^1$", May 1, 1993, pp. 4168–4178, The Journal of Immunology, vol. 150, No. 9.

Nicholas J. Lowe, "Psoriasis: In Vivo Models for Topical Drug Evaluation", Jan. 28, 1988, pp. 147–155, Drug Development Research, vol. 13.

Elaine Fuchs, "Keratin genes, epidermal differentiation and animal models for the study of human skin diseases" Biochem Soc. Transactions, 19(4):1112–1115 (1991).

Nickoloff, B. J., "Severe Combined Immunodeficiency Mouse and Human Psoriatic Skin Chimeras—Validation of a New Animal Model", Amer. Journal of Pathology, vol. 146(3) (1995).

Carroll, J. M., et al., "Suprabasal Integrin Expression in the Epidermis of Transgenic Mice Results in Developmental Defects and a Phenotype Resembling Psoriasis", Cell, 83:957–968 (1995).

Groves, R. W., et al., "Inflammatory skin disease in transgenic mice that express high levels of interleukin 1α in basal epidermis", Proc. Natl. Acad. Sci. USA, 92:11874–11878 (1995).

Hammer, R. E., et al., "Spontaneous Inflammatory Disease in Transgenic Rats Expressing HLA–B27 and Human $\beta_2$m: An Animal Model of HLA–B27–Associated Human Disorders", Cell, 63:1099–1112 (1990).

Wilson, J. B., et al., "Expression of the BNLF–1 Oncogene of Epstein–Barr Virus in the Skin of Transgenic Mice Induces Hyperplasia and Aberrant Expression of Keratin 6", Cell, 81:1315–1327 (1990).

M. Schön et al. Nature Medicine 3(2) 183–8 ('97).
D. Bullard et al. PNAS 93: 2116–2121 ('96).
H. Williams et al. Dermatology 189(3) 238–240 ('94).
D. Greiner et al. Am. J. Pathology 146(4) 888–902 ('95).
T. Steinsuik et al. Scand. J. Immunol. 42(6) 607–16 ('95).
P. Van Horssen et al. Intl. J. Cancer 68(3) 378–83 (96).
A. Kawata et al. Cancer Res. 54(10) 2688–94 ('94).
G. Arreaza et al. J. Clin. Endocrin. & Merab. 80(12) 3724–31 ('95).
T. Itoh et al. Cancer 72(9) 2686–94 ('93).
C. Lezama–Davila, et al Memorias do Instituto Oswaldo Cruz Rio de Janiero 90(1) '95 pp. 51–58.
M. Birkeland et al. PNAS 86: 6734–8 '89.

*Primary Examiner*—Deborah Crouch
*Assistant Examiner*—Jill D. Martin
*Attorney, Agent, or Firm*—Wolf, Greenfield & Sacks, P.C.

[57] ABSTRACT

Methods and compositions for preparing a mouse model of an inflammatory skin condition are disclosed. The methods involve administering donor lymphocytes to a recipient immune deficient mouse to induce the inflammatory skin response. The mouse models are useful for testing the efficacy of a therapeutic agent for treating the inflammatory skin condition. In particular, the mouse models are useful for screening therapeutic agents for treating human psoriasis.

23 Claims, 3 Drawing Sheets

MOUSE MODEL OF PSORIASIS

GOVERNMENT SUPPORT

The invention described herein was supported in part by a grant from the National Institute of Health. The government retains certain rights in this invention.

FIELD OF THE INVENTION

This invention relates to methods and compositions for preparing an animal model of an inflammatory skin condition. In particular, the invention relates to methods and compositions for preparing a murine model of psoriasis.

BACKGROUND OF THE INVENTION

Psoriasis is one of the most frequent skin diseases, affecting 1–3% of the Caucasian population worldwide (Barker, J. N. W. N., (1994), Bailliere's Clin. Rheumatol. 8, 429–437.). This complex disease is characterized by alterations in a variety of different cells. These include epidermal keratinocyte hyperproliferation and altered differentiation indicated by focal parakeratosis (cell nuclei in stratum corneum), aberrant expression of the hyperproliferation-associated keratin pair 6/16 (Stoler, A., et al., (1988), J. Cell Biol. 107, 427–446; Weiss, R. A., et al., (1984), J. Cell Biol. 98, 1397–1406), involucrin and filaggrin (Bernard, B. A. et al., (1986), Br. J. Dermatol. 114, 279–283; Dover, R. and Watt, F. M., (1987), J. Invest. Dermatol. 89, 349–352.; Ishida-Yamamnoto, A. and Iizuka, H., (1995), J. Invest. Dermatol. 104, 391–395), and integrin adhesion molecules (VLA-3, 5 and 6, $\alpha^6\beta_4$) (Hertle, M. D., et al., (1992), J. Clin. Invest. 89, 1982–1901; Kellner, J., et al., (1992), Br. J. Dermatol. 125, 211–215). In addition, de-novo expression of major histocompatibility complex (MHC) class II and intercellular adhesion molecule-1 (ICAM-1, CD54) by keratinocytes is observed (Barker, J. N. W. N., et al., (1990), J. Clin. Invest. 85, 605–608; Gottlieb, A. B., et al., (1986), J. Exp. Med. 164, 1013–1028; Griffiths, C. E. M., et al., (1989), J. Am. Acad. Dermatol. 20, 617–629; Nickoloff, B. J., et al., (1990), J. Invest. Dermatol. 94, 151S–157S; Veale, D., et al., (1995), Br. J. Deimatol. 132, 32–38). Endothelial cells also are hyperproliferative resulting in angiogenesis and dilation (Detmar, M., et al., (1994), J. Exp. Med. 180, 1141–1146; Goodfield, M., et al., (1994), Br. J. Dermatol. 131, 808–813; Malhotra, R., et al., (1989), Lab. Invest. 61, 162–168; Mordovtsev, V. N. and Albanova, V. I., (1989), Am. J. Dermatopathol. 11, 33–42) and express increased levels of ICAM-1, E-selectin (CD62E) and vascular cell adhesion molecule-1 (VCAM-1, CD106) (Das, P. K., et al., (1994), Acta Derm.Venereol. Supplementum 186, 21–22) as well as MHC class II (Bjerke, J. R., et al., (1988), Acta Derm. Venereol. 68, 306–311). Finally, a mixed leukocytic infiltrate is seen composed of activated T-lymphocytes which produce inflammatory cytokines (Ramirez-Bosca, A., et al., (1988), Br. J. Dermatol. 119, 587–595; Schlaak, J. F., et al., (1994), J. Invest. Dermatol. 102, 145–149), neutrophils within the dermis and formning Munro's microabscesses in the epidermis (Christophers, E., and Sterry, W. (1993). Psoriasis. In Dermatology in General Medicine, T. B. Fitzpatrick, A. Z. Eisen, K. Wolff, I. M. Freedberg and K. F. Austen, eds. (New York: McGraw-Hill, Inc.), pp. 489–514.), and an increased number of dermal mast cells (Brody, I., (1986), Upsala J. Med. Sci. 91, 1–16; Brody, I., (1984), J. Invest. Dermnatol. 82, 460–4; Rothe, M. J., et al., (1990), J. Am. Acad. Dermatol. 23, 615–24; Schubert, C. and Christophers, E., (1985), Arch. Dermatol. Res. 277, 352–358; Toruniowa, B. and Jablonska, S. (1988), Arch. Dermatol. Res. 280, 189–193; van de Kerkhof, P. C., et al., (1995), Skin Pharmacol. 8, 25–29). Intracutaneous secretion of cytokines is thought to mediate some or all of the tissue alterations seen in psoriasis. These cytokines include tumor necrosis factor-$\alpha$ (TNF$\alpha$) and interleukin-1 (IL-1) (Kupper, T. S., (1990), J. Clin. Invest. 86, 1783–1786); interferon-$\gamma$ (IFN$\gamma$) (Barker, J. N. W. N., et al., (1991), J. Dermatol. Sci. 2, 106–111; Gottlieb, A. B., et al., (1988), J. Exp. Med. 167, 670–675; Livden, J. K., et al., (1989), Arch. Dermatol. Res. 281, 392–397), IL-6 (Castells-Rodellas, A., et al., (1992), Acta Derm.Venereol. 72, 165–168; Grossman, R. M., et al., (1989), Proc. Natl. Acad. Sci. USA 86, 6367–6371; Neuner, P., et al., (1991), J. Invest. Dermatol. 97,27–33), IL-8 (Barker, J. N., et al., (1991), Am. J. Pathol. 139, 869–876), vascular endothelial growth factor/vascular permeability factor (VEGF/VPF) (Detmar, M., et al., (1994), J. Exp. Med. 180, 1141–1146), and transforming growth factor-$\alpha$ (TGF$\alpha$) (Elder, J. T., et al., (1989), Science 243, 811–814; Gottlieb, A. B., et al., (1988), J. Exp. Med. 167, 670–675; Prinz, J. C., et al., (1994), Eur. J. Immunol. 24, 593–598).

Over the past decade, research into the pathophysiology of psoriasis has focused primarily on immunologic mechanisms and evidence is accumulating that this disease has an immunological basis. However, it has not been convincingly determined if the primary defect that results in psoriasis is an immunologic disorder or resides within the epithelium (Barker, J. N. W. N., (1994), Bailliere's Clin. Rheumatol. 8, 429–437; Christophers, E., and Sterry, W. (1993). Psoriasis. In Dermatology in General Medicine, T. B. Fitzpatrick, A. Z. Eisen, K. Wolff, I. M. Freedberg and K. F. Austen, eds. (New York: McGraw-Hill, Inc.), pp. 489–514). Abnormal immune regulation is suggested by the frequent association of psoriasis with the expression of certain MHC alleles including –B13, –B17, –Bw57 and –Cw6 (Russell, T. J., et al., (1972), N. Engl. J. Med. 287, 738–740; Tiilikainen, A., et al., (1980), J. Dermatol. 102, 179; Watson, W., et al., (1972), Arch. Dermatol. 105, 197–207; White, S. H., et al., (1972), N. Engl. J. Med. 287, 740–743), the improvement of psoriatic lesions by treatment with immunosuppressive agents such as cyclosporin A (Ellis, C. N., et al., (1986), J. Am. Med. Assoc. 256, 3110–3116; Mueller, W. and Herrmann, B., (1979), N. Engl. J. Med. 301, 555) and the lymphocyte-specific toxin DAB389 IL-2 (Gottlieb, J. L., et al., (1995), Nature Med. 1, 442–447), the possible linkage of a psoriasis susceptibility gene with a gene involved in IL-2 regulation (Tomfohrde, J., et al., (1994), Science 264, 1141–1145), and the failure of psoriasis to recur after bone marrow transplantation (Eedy, D. J., et al., (1990), Br. Med. J. 300, 908; Jowitt, S. N., et al., (1990), Br. Med. J. 300, 1398–1399). However, underlying epidermal and/or dermal defects are suggested by altered keratinocyte cell cycle and differentiation (Gelfant, S. (1982), Cell Tissue Kinet. 15, 393–397; Weinstein, G. D., et al., (1985), J. Invest. Dermatol. 84, 579–583), by aberrant expression of adhesion molecules by keratinocytes and endothelial cells (Das, P. K., et al., (1994), Acta Derm.Venereol. Supplementum 186, 21–22; Nickoloff, B. J., et al., (1990), J. Invest. Dermatol. 94, 151S–157S; Petzelbauer, P., et al., (1994), J. Invest. Dermatol. 103, 300–305; Veale, D., et al., (1995), Br. J. Dermatol. 132, 32–38; Wakita, H. and Takigawa, M., (1994), Arch. Dermatol. 130, 457–463), and by the abnormal expression of protooncogenes within keratinocytes (Elder, J. T., et al., (1990), J. Invest. Dermatol. 94, 19–25).

Research into the pathogenesis underlying the complex and intertwined alterations in psoriatic skin lesions has been severely hampered by the lack of appropriate animal models (Grammer, S. F., and Streilein, J. W. (1994), The immune system in cutaneous disease: the search for a mouse model of the immunopathology of psoriasis. In Handbook of mouse mutations with skin and hair abnormalities. Animal models and biomedical tools., J. P. Sundberg, ed. (Boca Raton, Ann Arbor, London, Tokyo: CRC Press), pp. 143–153; Nickoloff, B. J., et al., (1995), Am. J. Pathol. 146, 580–588: Vallat, V. P., et al., (1994), J. Exp. Med. 180, 283–296). Several investigators have produced transgenic animals in which increased expression of cytokines, adhesion molecules or other proteins in the skin results in epithelial hyperproliferation and altered differentiation (Carroll, J. M., et al., (1995), Cell 83, 957–968; D'Armiento, J., et al., (1995), Mol. Cell. Biol. 15, 5732–5739; Groves, R. W., et al., (1995), Proc. Natl. Acad. Sci. USA 92, 11874–11878; Guo, L. et al., (1993), EMBO J. 12, 973–986; Hammer, R. E., et al., (1990), Cell 63, 1099–1112; Takahashi, K., et al., (1994), J. Cell Biol. 127, 505–520; Vassar, R. and Fuchs, E., (1991), Genes Dev. 5, 714–727; Wilson, J. B., et al., (1990), Cell 61, 1315–1327). In some of these animals, an inflammatory reaction and/or dilation of blood vessels also occur in response to alterations in the epidermis (Groves, R. W., et al., (1995), Proc. Natl. Acad. Sci. USA 92, 11874–11878; Wilson, J. B., et al., (1990), Cell 61, 1315–1327; Carroll, J. M., et al., (1995), Cell 83, 957–968; Hammer, R. E., et al., (1990), Cell 63, 1099–1112). In addition, several mice with spontaneous mutations develop some features like those seen in human psoriasis (Grammer, S. F., and Streilein, J. W. (1994), The immune system in cutaneous disease: the search for a mouse model of the immunopathology of psoriasis. In Handbook of mouse mutations with skin and hair abnormalities. Animal models and biomedical tools., J. P. Sundberg, ed. (Boca Raton, Ann Arbor, London, Tokyo: CRC Press), pp. 143–153; Sundberg et al., (1993), Immunol. Invest. 22:389–401; Sundberg et al., (1990), J. Invest. Dermatol. 95:62s–63s; Brown and Hardy, (1988), Clin. Exp. Dermatol. 13:74–77; Gates and Karasek, (1965), Science 148:1471–1473; HogenEsch et al., "The chronic proliferative dermatitis (cpd) mutation, chromosome?" In: Handbook of mouse mutations with skin and hair abnormalities, Animal models and biomedical tools, J. P. Sundberg (ed.), CRC Press, Boca Raton, pp. 217–220 (1994).

Of note, one animal model has been produced which reportedly results from a primary immunologic abnormality. Expression of human HLA-B27 and $\beta_2$ microglobulin in transgenic rats (HLA-B27 transgenic rats) reportedly results in the development of inflammation at many sites, including the gastrointestinal tract, joints, male genital tract, heart and skin (Hammer, R. E., et al., (1990) Cell 63:1099–1112). While some features of psoriasis are reported to occur in the skin of these HLA-B27 transgenic rats, others have not been noted, including dermal angiogenesis and blood vessel dilation as well as cutaneous mast cell infiltration. In addition, even for those HLA-B27 transgenic lines expressing the highest copy number, the skin changes reportedly did not appear until the animals were eighteen weeks old. Moreover, in one of these high copy number transgenic lines, reportedly only 50% of the transgenic animals were affected as late as twenty-five weeks of age (Taurog, J. D., et al., (1993) J. Immunol. 150:4168–4178). Thus, the transgenic HLA-B27 model is inadequate for screening therapeutic agents for treating an inflammatory skin condition because the skin changes reported for the HLA-B27 transgenic lines only occur in more mature animals with only moderate frequency. In another animal model reported for psoriasis, human psoriatic skin is transplanted onto the skin of a scid mouse. In these animal models, the transplanted skin grafts reportedly implant with greater than 85% graft survival and continued to exhibit psoriatic features for at least six weeks after transplantation (Nickoloff, B. J., et al., (1995), Amer. J. Pathol. 146:580–588; Boehncke, W.-H., et al., (1994), Arch. Dermatol. Res. 286:325–330). However, this animal model is difficult to utilize as a screening method for therapeutic agents as it requires human skin for transplantation to generate the model. Thus, there are no prior models of psoriasis in which the clinical and histopathological phenotype are known to develop as the result of a primary immunologic abnormality, in which 100% of the animal models are affected within two months and which do not require the use of human skin for model generation.

In view of the foregoing, there is still a need for an improved model for screening agents that are useful for treating an inflammatory skin condition. In particular, there is still a need for an improved model for psoriasis, which model mimics the immunopathological basis of psoriasis, occurs rapidly in virtually all test animals, and does not require the use of human skin to generate the model.

SUMMARY OF THE INVENTION

The present invention overcomes the problems of the prior art by providing an improved model of an inflammatory skin condition. Unlike the models of the prior art, the model of the present invention mimics the clinical and histopathologic characteristics of human psoriasis, is immunologically based and occurs within seventy days in virtually all experimental animals. Accordingly, the model disclosed herein is useful for studying the immunopathogenesis of inflammatory skin conditions, such as human psoriasis, and for evaluating therapeutic agents for ameliorating or preventing such conditions.

The compositions and the methods of the invention are based upon the recognition that reconstitution of an immune deficient animal (e.g., an animal lacking functional T-lymphocytes) with a selected subset of T-lymphocytes induces an inflammatory skin condition that closely resembles human psoriasis. In particular, the animal model of the invention has in common with human psoriasis the following clinical and histopathological features: dermal and epidermal infiltration of T lymphocytes in association with erythematous skin with loose whitish scales, acanthosis, hyperkeratosis and focal parakeratosis, keratinocyte hyperproliferation, changes in epidermal differentiation markers, and increased expression of MHC class II and ICAM-1, prominent dermal angiogenesis and dilation of blood vessels, increased number of dermal mast cells, and infiltration of neutrophils in the dermis with formation of microabscesses within the epidermis. Striking parallels between the animal model and human psoriasis also were observed in the pattern of cytokine expression. As in human psoriatic skin, production of the inflammatory cytokines gamma-interferon TNFα, as well as IL-1, VEGF, GM-CSF, and IL-6 was dramatically increased in the animal model compared to immune deficient animals which had not been reconstituted with the selected subset of T-lymphocytes disclosed herein. In summary, although other animal models have been reported for human psoriasis, the animal model of the invention represents the first in vivo experimental system which has an immunopathological basis, can be induced in virtually all experimental animals within seventy days, and does not require the use of human skin for model generation. Thus, the animal model disclosed herein is not a transgenic animal model or a disease-affected skin transplantation animal model of an inflammatory skin condition.

According to one aspect of the invention, a method of preparing an animal model of an inflammatory skin condition is provided. The method involves administering a sufficient number of donor lymphocytes to a recipient animal to mediate the inflammatory skin condition and allowing the inflammatory skin condition to develop. The recipient animal is immune system deficient, i.e., the recipient animal is impaired in effecting a cellular immune system response, for example, because the recipient animal lacks functional T-lymphocytes. The donor lymphocytes are matched to the major histocompatibility complex of the recipient animal. The donor lymphocytes can be matched or mismatched to the minor histocompatibility antigens of the recipient animal.

The preferred inflammatory skin condition that can be induced using the foregoing method is psoriasis. Other skin conditions that share the primary pathogenic role of T cells with the model disclosed herein include eczema (e.g., contact dermatitis, atopic dermatitis, and nummular eczema), para-psoriasis, psoriasis associated with immune deficiency (for example, HIV infection) and some cutaneous T cell lymphomas. Thus, these conditions are likely to respond to the same therapeutic strategies that are useful in treating the animal model of psoriasis disclosed herein. The invention also is useful for inducing a psoriatic arthritis-like condition (i.e., an animal model of human psoriatic arthritis). Accordingly, the method of the invention is useful for preparing an animal model of the foregoing inflammatory conditions for use as a screening method for identifying therapeutic agents for treating these and related conditions. In general, the recipient animal is an immune system deficient rodent, such as a mouse or a rat. In the particularly preferred embodiments, the recipient animal is a mouse. More particularly, the recipient animal is selected from the group consisting of a scid mouse, an athymic rodent, an irradiated rodent, a RAG-2 deficient rodent, a CD-3 deficient rodent, a TCR$\alpha\beta$ deficient rodent and a T cell signaling defective rodent. A T cell signaling defective animal is an animal in which its T cells are unable to be fully activated by a T cell receptor-triggered signal. T cell signaling defective animals may lack functional molecules important in transmitting T cell receptor-triggered signals (e.g., ZAP-70, syk, fyn) or T cell accessory molecule-triggered signals (e.g., lck, CD4, CD8, CD2, integrin $\alpha^L\beta_2$ (LFA-1), CD28). T cell signaling defective animals can be identified by assaying T cells obtained from a putative T cell signaling defective animal for impaired proliferation, cytotoxic activity and/or cytokine release.

A sufficient number of donor lymphocytes are administered to the recipient to induce an inflammatory skin condition in which both the location and type of inflammatory cells infiltrating the skin are similar to the location and type of inflammatory cells which are seen in human psoriatic lesions. In contrast to the prior art animal models of inflammatory skin conditions, the methods of the invention induce the inflammatory skin condition in virtually all recipient animals (i.e., greater than 75% of the recipient animals) within seventy days of administration of the donor lymphocytes to the recipient animal. In general, the methods of the invention induce the inflammatory skin condition in greater than 90% of the recipient animals within thirty-five days of administration of the donor lymphocytes to the recipient animal. In most cases, the methods of the invention induce the inflammatory skin condition in 100% of the recipient animals. The methods of the invention are useful for preparing an animal model of an inflammatory skin condition in any immune deficient animal (preferably a rodent), regardless of the nature of the immune system deficiency (e.g., genetically or surgically manipulated, irradiation-induced or naturally occurring).

It is particularly preferred that the donor lymphocytes be major histocompatibility matched to the major histocompatibility complex of the recipient animal, i.e., the MHC loci of the recipient animal are identical to the MHC loci of the animal from which the donor lymphocytes are derived. By convention, non-MHC loci are considered minor histocompatibility complex antigens. These antigens may or may not be matched to those of the recipient animal. In general, the donor lymphocytes are integrin $\alpha^E$ (CD103) deficient or wild-type T-lymphocytes (e.g., splenocytes, naive T-lymphocytes, or CD45RB$^{hi}$ T-lymphocytes) which may be either unfractionated or a subset (e.g., CD4$^+$, CD8$^+$ or CD4$^-$/CD8$^-$). Thus, exemplary donor lymphocytes include $\alpha^E$ deficient splenocytes, $\alpha^E$ deficient naive CD4$^+$ T-lymphocytes, $\alpha^E$ deficient CD4$^+$/CD45RB$^{hi}$ T-lymphocytes, $\alpha^E$ deficient naive CD8$^+$ T-lymphocytes, naive CD4$^+$ T-lymphocytes, naive CD8$^+$ T-lymphocytes, naive CD4$^-$/CD8$^-$ T-lymphocytes, $\alpha^E$ deficient naive CD4$^-$/CD8$^-$ T-lymphocytes and $\alpha^E$ wild-type CD4$^+$/CD45RB$^{hi}$ T-lymphocytes. In the particularly preferred embodiments, the donor lymphocytes are $\alpha^E$ deficient naive CD4$^+$ T-lymphocytes (e.g., $\alpha^E$ deficient CD4$^+$/CD45RB$^{hi}$ T-lymphocytes).

According to yet another aspect of the invention, the above-described animal model is useful in a method of testing the efficacy of a therapeutic agent for treating an inflammatory skin condition. The method involves: (1) evaluating the symptoms of the inflammatory skin condition in at least one animal model of the invention; (2) contacting the at least one animal model with one or more therapeutic agents; and (3) re-evaluating the symptoms of the inflammatory skin condition in the at least one animal model. The order of performing steps (1) and (2) is not limited to the sequence provided, i.e., the at least one animal model can be contacted with the putative therapeutic agent(s) prior to induction or development of the inflammatory skin condition, to evaluate the efficacy of the therapeutic agent(s) as prophylactic agent(s) for preventing the condition. The prevention or amelioration of one or more symptoms in the animal model indicates that the therapeutic agent, alone or in combination with another therapeutic agent, is efficacious for treating the inflammatory skin condition. Evaluation of the symptoms of the inflammatory skin condition is by clinical assessment (including, e.g., serum cytokine measurement) and/or histopathology (including, e.g., immunopathology). Exemplary classes of putative therapeutic agents which can be tested in accordance with the methods of the invention include immunosuppressive agents, cytostatic agents, retinoids, tar and related compounds, anthralines, vitamin D3 analogues, ultraviolet irradiation (with or without one or more photosensitizing agents such as a psoralen) and agents which specifically inactivate or antagonize the action of cytokines, adhesion molecules (e.g., integrins, selecting, cadherins, functionally active fragments of the foregoing molecules or other inhibitors thereof which block the binding of these molecules to their respective ligands) or other molecules important in lymphocyte activation or function (e.g., CD2, CD28, B7-1, B7-2) which are involved in mediating the inflammatory skin condition. (See, e.g., PCT application no. PCT/US95/02044, publication no. WO 95/22610, entitled "Novel Integrin Alpha Subunit", for a description of functionally active fragments of the integrin alpha subunit.) The putative therapeutic agents are contacted with the animal model in accordance with known methods for testing agents for efficacy including, for example, topical, systemic, intracutaneous, intraperitoneal, and irradiation administration. As used herein, "contacting" embraces directly administering (e.g., topical, systemic, oral, irradiation of the animal) and indirectly administering (e.g., treatment of blood or blood components of the animal or donor cells with the therapeutic agent and/or ultraviolet irradiation (photopheresis) in the presence or absence of a psoralen) the therapeutic agent to the animal.

According to yet another aspect of the invention, the animal models produced by the above-described processes are provided. The animal models of the invention are useful for testing the efficacy of putative therapeutic agents for treating an inflammatory skin condition, as well as for characterizing the immunopathological mechanism underlying psoriasis and related immune system mediated disorders (e.g., benign and malignant T cell disorders which are characterized by the migration of T-lymphocytes to the skin). The animal models disclosed herein are distinct from the animal models debelibed in the prior art in several respects (described below). Significantly, the methods disclosed herein are useful for inducing an inflammatory skin condition in any immune system deficient animal. Accordingly, the animal models of the invention are not limited to transgenic animals such as those described in PCT application no. PCT/US90/03510, publication no. WO 90/15869, entitled "Transgenic Skin-Testing Systems" and PCT application no. PCT/US94/01674, publication no. WO 94/23760, entitled "Transgenic Animal Model for Autoimmune Diseases". Further in contrast to the prior art, the animal models disclosed herein mimic the spectrum of clinical and histopathologic symptoms of human psoriatic disease, can be induced in virtually all recipient animals within seventy days and does not require the use of human skin for model generation.

In its simplest form, the animal model of the invention is represented by an immune deficient recipient animal to which a sufficient number of donor lymphocytes have been administered to induce in the recipient animal an inflammatory skin condition. Donor lymphocytes that are useful for this purpose include $\alpha^E$ (CD 103) deficient or wild-type T-lymphocytes (e.g., splenocytes, naive T-lymphocytes, or CD45RB$^{hi}$ T-lymphocytes) which may be either unfractionated or a subset (e.g., CD4$^+$, CD8$^+$ or CD4$^-$/CD8$^-$). In the particularly preferred embodiments, the donor lymphocytes are $\alpha^E$ deficient naive CD4+ T-lymphocytes (e.g., $\alpha^E$ deficient CD4$^+$/CD45RB$^{hi}$ T-lymphocytes). Preferably, the donor lymphocytes optionally are isolated to contain a single subpopulation of T-lymphocytes. However, donor lymphocytes contained in a mixed population (e.g., splenocytes isolated from an $\alpha^E$ deficient animal (e.g., a knockout mouse) also are useful for achieving the purposes of the invention. In the preferred embodiments, the immune deficient animal is a mouse and the donor lymphocytes are $\alpha^E$ deficient splenocytes (more particularly, $\alpha^E$ deficient CD4$^+$/CD45RB$^{hi}$ T-lymphocytes) or CD4$^+$/CD45RB$^{hi}$ T-lymphocytes (more particularly, CD4$^+$/CD45RB$^{hi}$ T-lymphocytes from F$_2$(Balb/cJ×129/SvJ)H-2$^d$. The preferred $\alpha^E$ deficient lymphocytes can be obtained from an $\alpha^E$ knockout animal such as the animal disclosed in PCT application no. PCT/US95/02044, publication no. WO 95/22610, entitled "Novel Integrin Alpha Subunit". Alternative $\alpha^E$ knockout animals can be prepared in accordance with standard procedures known to those of ordinary skill in the art using the published sequence for integrin $\alpha^E$ (CD 103) (See, e.g., Smith, T., et al., Immunity 1:393–403 (1994)).

The animal model of the invention exhibits, within about seventy days (more preferably, within thirty-five days) following administration of the donor lymphocytes, cutaneous lymphocyte infiltration and at least 75% of the following symptoms (hereinafter, "symptoms substantially similar to human psoriatic disease"): (1) erythematous skin with loose whitish scales; (2) acanthosis, hyperkeratosis and focal parakeratosis; (3) keratinocyte hyperproliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit substantially the same trends (i.e., the same increasing or decreasing pattern of cytokine expression) as the changes in cytokine expression patterns that are reported in the skin of human patients with psoriasis. According to a particularly preferred embodiment described in the Examples, the preferred animal model exhibits at least 90% (more preferably, 100%) of the above-listed symptoms within about thirty-five days following administration of the donor lymphocytes.

According to yet another aspect of the invention, isolated donor lymphocytes for use in accordance with the methods of the invention are provided. The isolated donor lymphocytes are $\alpha^E$ (CD 103) deficient or wild-type T-lymphocytes (e.g., splenocytes, naive T-lymphocytes, or CD45RB$^{hi}$ T-lymphocytes) which may be either unfractionated or a subset (e.g., CD4$^+$, CD8$^+$ or CD4$^-$/CD8$^-$). In the particularly preferred embodiments, the donor lymphocytes are $\alpha^E$ deficient naive CD$^+$ T-lymphocytes (e.g., $\alpha^E$ deficient CD4$^+$/CD45RB$^{hi}$ T-lymphocytes).

In a particularly preferred embodiment, the isolated donor lymphocytes are contained in a container which includes a single dose of donor lymphocytes for administration to an immune system deficient recipient animal. The single dose of donor lymphocytes is sufficient to induce in the recipient animal, within 70 days following administration thereto, cutaneous lymphocyte infiltration with at least 75% of the above-described symptoms indicative of human psoriatic disease. Preferably, the container contains a sufficient number of donor lymphocytes to induce in each animal, at least 90% (more preferably, 100%) of these symptoms within 35 days following their administration to the recipient animal. In the most preferred embodiment, isolated $\alpha^E$ deficient donor lymphocytes (more preferably, $\alpha^E$ deficient naive CD4$^+$ T-lymphocytes) are provided, preferably within a container which contains a single dose as described above. However, other preparations of donor lymphocytes for inducing the inflammatory skin condition can be provided in isolated form (i.e., removed from their naturally-occurring environment within an animal).

These and other aspects of the invention, as well as various advantages and utilities, will be more apparent with reference to the drawings and to the detailed description of the preferred embodiments which follows. All patents, patent publications and references identified in this document are incorporated in their entirety herein by reference.

DETAILED DESCRIPTION OF THE INVENTION

Figure 1A:
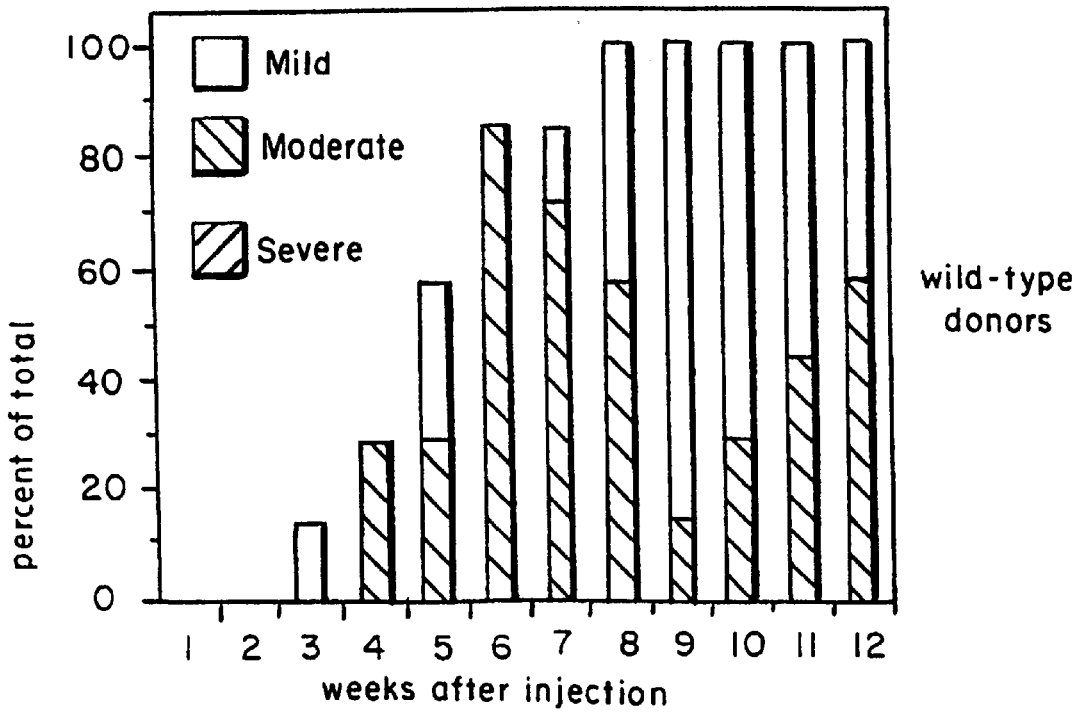
FIGS. 1A and 1B: Induction of psoriasiform skin lesions in C.B-17$^{scid/scid}$ mice. Onset and development of erythrosquamous skin lesions in recipient scid mice. Mice were injected with 2.45×10$^5$ CD4$^+$CD45RB$^{hi}$ T-cells from F$_2$ (Balb/cJ×129/SvJ)H-2$^d$ donors isolated from wild-type (FIG. 1A) or $\alpha^E$ deficient (FIG. 1B) donors. The overall heights of the bars represent the total number of affected animals per group, and the pattern indicates the severity of the skin disorder as assessed by the clinical score white—level I (mild disease), cross-hatched—level II (moderate disease) and speckled—level III (severe disease).
Figure 1B:
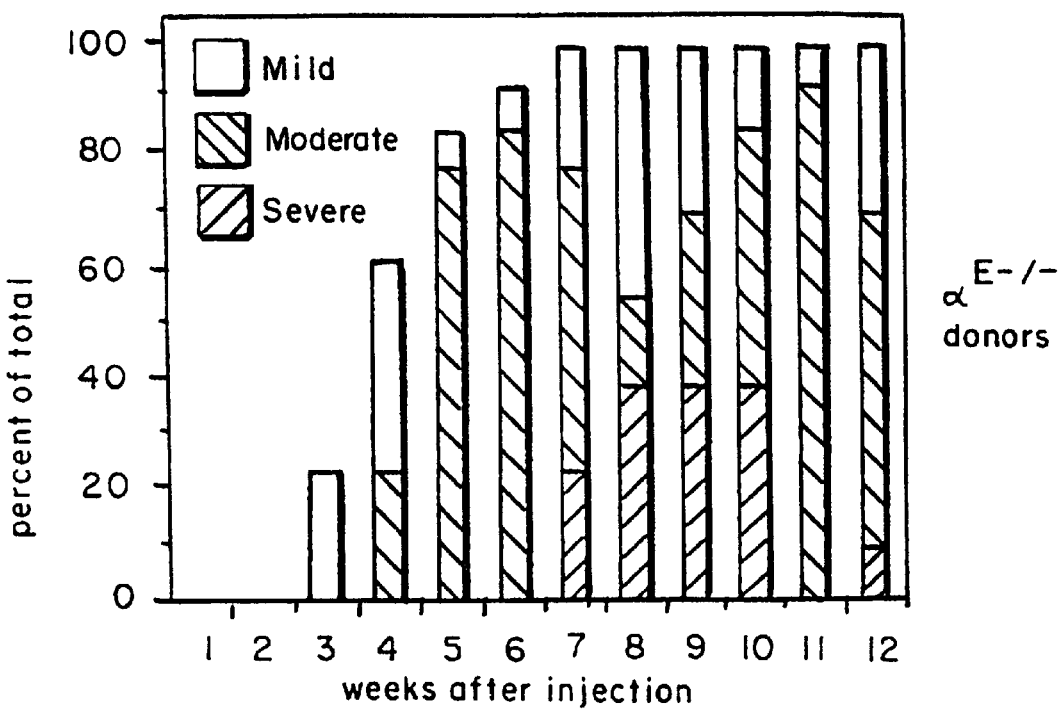

The instant invention embraces methods and compositions for preparing an animal model of an inflammatory skin condition and the animal models produced thereby. In contrast to the animal models available to date, the model of the invention mimics the clinical and histopathologic characteristics of human psoriasis, has an immunopathological basis, is characterized by consistent induction in virtually all (greater than 75%) recipient animals within about two months following administration of the donor lymphocytes and does not require human skin for model generation. Accordingly, the model disclosed herein is useful for studying the immunopathogenesis of inflammatory skin conditions and for evaluating therapeutic agents for treating such conditions. Exemplary inflammatory skin conditions include psoriasis, eczema (e.g., contact dermatitis, atopic dermatitis, and nummular eczema), para-psoriasis and psoriasis associated with immune deficiency (for example, HIV infection). The model also is useful for evaluating therapeutic agents for treating related disorders such as psoriatic arthritis. In the preferred embodiments for testing the efficacy of a therapeutic agent, the inflammatory skin condition is psoriasis. The animal models of the invention also are useful for testing the efficacy of putative therapeutic agents for characterizing the immunopathological mechanism underlying these and other inflammatory skin conditions, as well as for screening putative therapeutic agents and characterizing the mechanisms of other immune system mediated disorders (e.g., benign and malignant T cell disorders which are characterized by the migration of T-lymphocytes to the skin).

According to one aspect of the invention, a method of preparing an animal model of an inflammatory skin condition is provided. The method involves: (1) administering a sufficient number of donor lymphocytes to a recipient animal to mediate the inflammatory skin condition and (2) allowing the inflammatory skin condition to develop. The recipient animal is an immune system deficient animal. As used herein, an "immune system deficient animal" refers to an animal whose cellular immune system response is impaired or absent. For example, the cellular immune system deficiency may be the result of the animal's inability to produce functional T-lymphocytes due to a natural mutation, irradiation or surgery (e.g., neonatal thymectomy). Alternatively, the cellular immune system deficiency may be the result of inhibition of the animal's T-lymphocyte activity by, for example, inhibiting the T-lymphocyte activity using antisense oligonucleotides or other genetic engineering methods to produce, for example, knockout mice lacking functional T-lymphocytes or by irradiating the animal with lethal or sublethal irradiation to produce an animal lacking functional T-lymphocytes.

Immune system deficient animals can be "reconstituted" by establishing in the animal a population of T-lymphocytes that is capable of proliferating and/or functioning in vivo. Although any mammal which is immune system deficient (induced, naturally occurring or genetically manipulated) can be used as a recipient animal of the invention, the preferred recipient animal is a rodent. A mouse model is preferred. More preferably, the recipient animal is a severe combined immune deficiency ("scid") mouse, a CD-3 deficient mouse, a TCRαβ deficient mouse or a T cell signaling defective mouse. Mice which are RAG-2, CD-3 or TCRαβ-deficient are mice which lack one or more of these functional proteins, respectively. A T cell signaling defective animal is an animal in which its T cells are unable to be activated by a T cell receptor-triggered signal. T cell signaling defective animals lack at least one functional molecule important in transmitting T cell receptor-triggered signals (e.g., ZAP-70 syk, fyn) or T cell accessory molecule-triggered signals (e.g., lck, CD4, CD8, CD2, integrin $\alpha^L \beta_2$ (LFA-1, CD11aCD18), CD28). T cell signaling defective animals can be identified by assaying T cells obtained from a putative T cell signaling defective animal for impaired proliferation, cytotoxic activity and/or cytokine release. The preferred mouse for achieving the purposes of the instant invention is a scid mouse, more preferably, a C.B-17$^{scid/scid}$ mouse.

In the preferred embodiments, the recipient animal is a rodent (e.g., mouse, rat, hamster, gerbil, rabbit) and the donor lymphocytes are matched to the major histocompatibility complex of the recipient animal and may be matched or mismatched to the minor histocompatibility antigens of the recipient animal. Alternatively, the donor lymphocytes can be mismatched to the major histocompatibility complex of the recipient animal and may be matched or mismatched to the minor histocompatibility antigens of the recipient animal. The donor lymphocytes are administered to the recipient animal in accordance with known methods for introducing cells into an animal. These include intravenous injection, retro-orbital injection, intra-arterial injection, intraperitoneal injection and subcutaneous injection. Preferably, the donor lymphocytes are intravenously injected into the recipient animal.

A sufficient number of donor lymphocytes are administered to the recipient animal to induce the inflammatory skin condition. This number of donor lymphocytes can be described in functional and/or numerical terms as follows. In functional terms, a sufficient number of donor lymphocytes is that number which is sufficient to induce a condition in the recipient animal in which both the location and the type of inflammatory cells infiltrating the skin are substantially the same as the location and type of inflammatory cells infiltrating the skin as reported in human psoriatic lesions. By "substantially the same" it is meant that the animal model of the invention, within seventy days following administration of the donor lymphocytes, exhibits infiltration of lymphocytes into the dermis or epidermis and at least 75% of the "symptoms substantially similar to human psoriatic disease": (1) erythematous skin with loose whitish scales; (2) acanthosis, hyperkeratosis and focal parakeratosis; (3) keratinocyte hyperproliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit substantially the same trends (i.e., the same increasing or decreasing pattern of cytokine expression) as the changes in cytokine expression patterns that are reported in the skin of human patients with psoriasis. The "changes in cytokine expression patterns" include, in particular, the changes in the expression of the cytokines gamma-interferon (IFNγ), interleukin-1alpha (IL-1α), granulocyte macrophage colony stimulating factor (GM-CSF), tumor necrosis factor-alpha (TNF-α), interleukins (IL), IL-2, IL-6, IL-8, and vascular endothelial growth factor/vascular permeability factor (VEGF/IVPF). The changes in cytokine expression patterns optionally further include the changes in the expression patterns of additional cytokines that exhibit, or are later identified and found to exhibit, a change in expression pattern in the skin of human patients with psoriasis. Fewer donor lymphocytes can be administered to the recipient animal provided that the number of donor lymphocytes is sufficient to induce in the recipient animal within seventy days following administration of the donor lymphocytes, cutaneous T cell infiltration with at least 75% of foregoing symptoms. However, in the most preferred embodiments (see the Examples), the animal models of the invention exhibit at least 90% (more preferably, 100%) of the foregoing symptoms within about thirty-five days following administration of the donor lymphocytes.

The animal models disclosed herein display substantially the same location and type of inflammatory cells infiltrating the skin as those seen in human psoriatic lesions. Surprisingly, in further contrast to the methods for forming the animal models of the prior art, the methods disclosed herein result in inducing the inflammatory skin condition in virtually every recipient animal to whom the donor lymphocytes are administered. These results are unexpected and could not have been predicted based upon the results reported for animal models which had received lymphocytes containing an HLA-B27 transgene for the purpose of inducing an inflammatory condition resembling B27-associated human disease in a rat model (Taurog, J., et al., J. Immunology 150:4168–4178 (1993); Breban, M., et al., J. Immunology 156:794–803 (1996)).

According to the particular methods disclosed in the Examples, the number of donor lymphocytes is selected to induce in virtually all recipient animals (i.e., greater than 75% of the recipient animals) cutaneous infiltration of T lymphocytes and at least 75% of the aboveidentified symptoms within about 35 days following administration of the donor lymphocytes to the recipient animal. (More preferably, the number of donor lymphocytes administered is selected to induce in each recipient animal, at least 90% (most preferably, 100%) of the above-identified symptoms within about 35 days following administration of the donor lymphocytes). In contrast, the animal models of the prior art do not exhibit an inflammatory skin condition that is representative of the clinical and histopathologic profile reported in human psoriatic disease, that can be attributed to a primary T-cell dysregulation, that is characterized by consistent induction in virtually all recipient animals within about two months following administration of the donor lymphocytes, and that does not require transplantation of human skin for model generation.

The number of donor lymphocytes that are required to induce the inflammatory skin condition also can be defined in numerical terms. In general, the number of donor lymphocytes sufficient to induce at least 75% of the above-identified symptoms in each recipient animal within 70 days of administration of the donor lymphocytes to the recipient animal is between about $1 \times 10^3$ and about $1 \times 10^8$ cells. However, to induce a higher percentage of symptoms more rapidly, it is preferred that between about $1 \times 10^4$ and about $3 \times 10^5$ cells be administered to the recipient animal. In the most preferred embodiments (i.e., animals models in which each recipient animal exhibits 90 to 100% of the above-identified symptoms within about thirty-five days), a sufficient number of donor lymphocytes is between about $1 \times 10^5$ and about $3 \times 10^5$ cells. The donor lymphocytes are matched to the major histocompatibility complex of the recipient animal and may or may not be matched to the minor histocompatibility antigens. By "matched to the major histocompatibility complex" it is meant that the major histocompatibility complex (MHC) loci of the recipient animal (e.g., the H-2 locus of the mouse including the subtypes $H-2^k$, $H-2^s$ and $H-2^d$, and the RT1 locus of the rat) are identical to the MHC loci of the animal from which the donor lymphocytes are obtained. The rat MHC class I locus is designated RT1A; the rat MHC class II locus (murine MHC1-A equivalent) is designated RT1B; the rat MHC class II (murine I-E equivalent) is designated RT1D. According to convention, other non-MHC loci (e.g., non-H-2 loci of the mouse, non-RT1 loci of the rat) give rise to the minor histocompatibility antigens.

In accordance with the preferred embodiments, the recipient animal is a mouse (preferably, a scid mouse such as C.B-17$^{scid/scid}$ and the donor lymphocytes are selected from the following group: $\alpha^E$ (CD 103) deficient or wild-type T-lymphocytes (e.g., splenocytes, naive T-lymphocytes, or CD45RB$^{hi}$ T-lymphocytes) which may be either unfractionated or a subset (e.g., CD4$^+$, CD8$^+$or CD4$^-$/CD8$^-$). In the particularly preferred embodiments, the donor lymphocytes are $\alpha^E$ deficient naive CD4$^+$ T-lymphocytes (e.g., $\alpha^E$ deficient CD4$^+$/CD45RB$^{hi}$ T-lymphocytes). The CD4$^+$/CD45RB$^{hi}$ T-lymphocytes are an exemplary subpopulation of naive CD4$^+$ lymphocytes that are matched to the major histocompatibility complex of the C.B-17$^{scid/scid}$ mouse (recipient animal), but are mismatched to the minor histocompatibility antigens of the recipient animal. Exemplary donor animal minor histocompatibility antigens which can be mismatched to the minor histocompatibility antigens of the recipient animal include antigens that are encoded by genes linked to the Igh locus or the H-40 encoding locus.

The above-identified procedures for preparing an animal model of an inflammatory skin condition can be further adapted for testing the efficacy of a therapeutic agent for treating the inflammatory skin condition. According to this aspect of the invention, a method of testing the efficacy of a therapeutic agent for treating an inflammatory skin condition is provided. The efficacy of a therapeutic agent for treating an inflammatory skin condition can be assessed in individual animals (e.g., by clinical and/or histopathologic evaluation) or in a representative sampling of animals (e.g., by clinical evaluation and/or histopathologic evaluation of groups of treated versus untreated or control treated animals). Thus, the invention provides a method for testing the efficacy of a putative therapeutic agent by comparing the treated and untreated groups of animals and observing whether the treated group of animals (i.e., the group which received the putative therapeutic agent) exhibits an improved clinical and/or histopathologic profile compared to a positive control (i.e., an animal model or group of animal models which received a drug known to be effective for treating the condition) and/or to a negative control (i.e., an animal model or group of animal models which received no treatment or treatment with an irrelevant agent). According to this aspect of the invention, the method of testing the efficacy of a therapeutic agent for treating an inflammatory skin condition involves three steps: (1) evaluating the symptoms of the inflammatory skin condition in at least one of the animal model of the invention; (2) contacting the at least one animal model with at least one therapeutic agent; and (3) re-evaluating the symptoms of the inflammatory skin condition in the at least one animal model. The order of performing steps (1) and (2) is not limited to the sequence provided, i.e., the at least one animal model can be contacted with the putative therapeutic agent prior to induction or development of the inflammatory skin condition, to evaluate the efficacy of a therapeutic agent as a prophylactic agent for preventing the condition. Thus, the animal models and methods of the invention also are useful for evaluating the therapeutic efficacy using two or more therapeutic agents in combination by contacting the animal model with one or more therapeutic agents (e.g., an immunosuppressive agent and irradiation) in accordance with the methods disclosed herein.

As used herein, "contacting" embraces directly administering (e.g., topical, systemic, oral, irradiation of the animal) and indirectly administering (e.g., treatment of blood or blood components of the animal or donor cells with the therapeutic agent and/or ultraviolet irradiation (photopheresis) in the presence or absence of a psoralen) the therapeutic agent. Prevention, delayed onset, or reduction of one or more of the above-described symptoms of the inflammatory skin condition in the animal model(s) which received the therapeutic agent(s) is indicative that the therapeutic agent is efficacious for treating the condition.

As used herein, "treating an inflammatory skin conditioN" refers to preventing, delaying the onset of, or reducing to a statistically significant extent, one or more symptoms of the inflammatory skin condition. Therapeutic agents for which efficacy can be tested using the animal models of the invention include: immunosuppressive agents; cytostatic agents; retinoids (e.g., etretinate, acitritin, and isotretinoin); tar and related compounds; anthralines; vitamin D3 analogues (e.g., calcipotriol); ultraviolet light irradiation (with or without one or more photosensitizing agents such as a psoralen (e.g., 8-methoxypsoralen); and agents which specifically inactivate or antagonize the action of cytokines, adhesion molecules or other molecules important in mediating the inflammatory skin condition (described above). Such cytokine inactivating agents further include antibodies to the cytokines, as well as antisense oligonucleotides which specifically bind under stringent conditions to the nucleic acids encoding the cytokines, as well as agents which block cytokine receptors. Exemplary stringent conditions are disclosed in PCT application no. PCT/US95/02044, publication no. WO 95/22610, entitled "Novel Integrin Alpha Subunit".

Exemplary categories of immunosuppressive agents which can be evaluated as therapeutic agents using the animal models of the invention include steroids (e.g., prednisone); cyclosporine (e.g., cyclosporin A); T-cell toxins (i.e., therapeutic agents which specifically target T-lymphocytes and which are toxic, e.g., antibodies covalently coupled to a cytotoxic agent) and agents which interfere with T-lymphocyte function (e.g., by preventing the migration of T-lymphocytes to the skin and/or by preventing T-lymphocyte function within the skin). Exemplary cytostatic agents include methotrexate, 5-fluorouracil and hexadecylphosphocholin. Exemplary T-cell toxins include IL-2 receptor targeted toxins such as DAB 389 IL2, an experimental drug currently in use for psoriasis treatment, as well as antibodies which are specifically reactive with T-cell populations and which further include a toxin for killing the T-cell following its recognition by the antibody. The animal models of the invention also are useful for screening molecular libraries (e.g., peptide libraries such as disclosed in U.S. Pat. No. 5,010,175, issued Apr. 23, 1991 to Rutter et al.), as well as libraries of small molecules such as disclosed in PCT application no. PCT/US95/00344, publication no. WO 95/19359, entitled "Process for Making Xanthene or Cubane Based Compounds, and Protease Inhibitors) to identify therapeutic agents contained therein that are useful for treating an inflammatory skin condition.

The therapeutic agent(s) is contacted with the animal model in accordance with standard practice, e.g., via topical, systemic, oral, intraperitoneal, intracutaneous and irradiation (for UV treatment) administration. The symptoms of the inflammatory skin condition are evaluated by clinical assessment and/or by histopathology. Clinical assessment of the therapeutic agent-treated animal model includes assessing the extent of erythema over the body surface and the severity of scaling; assessing ear thickness and the thickness of skin in other areas (e.g, the footpad, trunk skin) of the animal; performing procedures such as diaphanoscopy (light absorption through a skin portion) to assess the thickness and/or blood perfusion of the skin; and determining cytokine concentrations in, for example, blood samples or tissue biopsies taken from the animal model before and after treatment. Immunopathologic assessment of the efficacy of the putative therapeutic agent involves determining the number of proliferating cells in the dermis and/or the epidermis; determining the thickness of the epidermis; determining the density of leukocyte infiltrate; determining the expression of markers that are known by those skilled in the art to differentiate between a normal state and an inflammatory condition (e.g., MHC class II, ICAM-1, and epithelial differentiation antigens such as integrins, involucrin and cytokeratins); and determining an increase in the number and/or dilation of blood vessels (e.g., by microscopic examination). In general, clinical assessment and/or histopathology which indicate prevention, reduction or delayed onset of the above-listed symptoms of an inflammatory skin condition are indicative of a therapeutic agent which is efficacious for treating the condition. The methods of the invention also are useful for evaluating existing therapeutic strategies for treating psoriasis and related immune system mediated conditions. For example, the methods of the invention can be used to critically evaluate the efficacy of ultraviolet irradiation therapy alone or in combination with another therapeutic agent for treating an inflammatory skin disorder. Similarly, the methods of the invention can be used to evaluate photopheresis for efficacy in treating inflammatory skin conditions by irradiating the donor cells and/or the blood or blood components of the recipient animal with ultraviolet light in the presence or absence of a photosensitizing agent (e.g., a psoralen such as 8-methoxypsoralen, "8-MOP") and determining whether the treatment prevents, delays the onset of, or reduces to a statistically significant extent the development of the inflammatory skin condition. In this manner, the methods of the invention can be used to critically evaluate the efficacy of therapeutic strategies for treating inflammatory skin conditions and in particular, for evaluating the efficacy of these therapies for treating psoriasis.

According to yet another aspect of the invention, animal models produced by the above-described process are provided. In a particularly preferred embodiment, the animal model is an immune system deficient rodent (preferably a mouse or a rat) that has been reconstituted with a sufficient number of donor lymphocytes to exhibit a cutaneous lymphocyte infiltrate and at least 75% of the above-listed symptoms of an inflammatory skin condition within seventy days (more preferably, within thirty-five days) following administration of the donor lymphocytes to the recipient animal. The preferred animal models of the invention exhibit 90 to 100% of the above-listed symptoms within thirty-five days following administration of the donor lymphocytes to the recipient animal. The most preferred animal models are immune system deficient animals which have been reconstituted with MHC-matched donor lymphocytes that are selected from the following groups: $\alpha^E$ (CD 103) deficient or wild-type T-lymphocytes (e.g., splenocytes, naive T-lymphocytes, or CD45RB$^{hi}$ T-lymphocytes) which may be either unfractionated or a subset (e.g., CD4$^+$, CD8$^+$ or CD4$^-$/CD8$^-$). In the particularly preferred embodiments, the donor lymphocytes are $\alpha^E$ deficient naive CD4$^+$ T-lymphocytes (e.g., $\alpha^E$ deficient CD4$^+$/CD45RB$^{hi}$ T-lymphocytes). In the particularly preferred embodiments, the recipient animal is a C.B-17$^{scid/scid}$ mouse and the donor lymphocytes are $\alpha^E$ deficient naive CD4$^+$ T-lymphocytes (e.g., $\alpha^E$ deficient CD4$^+$/CD45RB$^{hi}$ T lymphocytes) or $\alpha^E$ wild-type naive CD4$^+$ T-lymphocytes (e.g., $\alpha^E$ wild-type CD4$^+$/CD45RB$^{hi}$ T lymphocytes) from an F$_2$(Balb/cJ×129/SvJ)H-2$^d$ mouse.

According to yet another aspect of the invention, a product including a container and donor lymphocytes contained therein is provided. The container contains a single dose of isolated donor lymphocytes for administration to an immune system deficient recipient animal. The single dose of donor lymphocytes is sufficient to induce in the recipient animal, within seventy days following administration, a cutaneous lymphocyte infiltrate and at least 75% of the above-listed symptoms of the inflammatory skin condition. In a particularly preferred embodiment, the container contains a sufficient number of $\alpha^E$ deficient CD4$^+$/CD45RB$^{hi}$ splenocytes to induce an inflammatory skin condition in an immune system deficient recipient animal. Typically, this number of splenocytes is between about 1×10$^3$ and about 1×10$^8$ splenocytes.

The instant invention provides methods and compositions for forming and using an animal model of an inflammatory skin condition. The following examples illustrate representative utilities of the instant invention.

EXAMPLES

Example 1
Induction of an Inflammatory Skin Condition in C.B-17$^{scid/scid}$ mice by administration of CD4$^+$/CD45RB$^{hi}$ T-lymphocytes.
A. Results
Induction of erythrosquamous skin lesions in C.B-17$^{scid/scid}$ mice It has been shown previously that injection of C.B-17$^{scid/scid}$ mice (H-2$^d$) with CD4$^+$/CD45RB$^{hi}$ T-lymphocytes derived from the immunoglobulin congenic strain Balb/cJ results in the development of a wasting syndrome associated with severe intestinal inflammation. (See, e.g., Powrie, et al. (Powrie, F. (1995), Immunity 3, 171–174; Powrie, F., et al., (1994), J. Exp. Med. 179, 589–600; Powrie, F., et al., (1993), Int. Immunol. 5, 1461–1471). Splenocytes were isolated from 5–6 F$_2$(Balb/cJ×129/SvJ)H-2$^d$ mice to increase the likelihood that the mismatched minor histocompatibility antigens would be consistently represented in subsequent experiments. The CD4$^+$ T-cells within the splenocyte population were enriched by magnetic bead selection to remove cells expressing the B220, MHC class II, integrin $\alpha^M$, and CD8 antigens. The cells were stained with CD4$^-$phycoerythrin and CD45RB-FITC and the 40% of CD4$^+$ cells expressing the highest levels of CD45RB and the 15–20% expressing the lowest levels were selected using a two-color FACS.

C.B-17$^{scid/scid}$ mice were injected with 2.45×10$^5$ cells of either the CD4$^+$/CD45RB$^{hi}$ (FIG. 1A) or the CD4$^+$/CD45RB$^{lo}$ population, or with a mixture of 2.45×10$^5$ CD4$^+$/CD45RB$^{hi}$ cells and 0.8×10$^5$ CD4$^+$/CD45RB$^{lo}$ cells (CD4$^+$/CD45RB$^{hi+lo}$).

As expected, mice injected with CD4$^+$/CD45RB$^{hi}$ T-lymphocytes derived from F$_2$(Balb/cJ×129/SvJ)H-2$^d$ developed a wasting syndrome and intestinal inflammation. Surprisingly, these mice also developed erythrosquamous skin lesions which were present in the ears of all animals and in the feet, tail or trunk of most animals. The skin alterations and weight loss appeared concurrently suggesting that the skin lesions were not secondary to the intestinal abnormalities. In fact, some animals developed skin lesions in the absence of weight loss. In six separate experiments, all animals followed for at least six weeks developed skin lesions. The severity of the erythrosquamous skin disorder varied from mild erythema and scaling affecting only the ears to severe erythroderma and scaling extending over most or all of the body surface. As these skin lesions were not reported when Balb/cJ mice were used as donors, it seemed possible that the lesions were due to a minor histocompatibility antigen mismatch graft-versushost-disease resulting from the use of F$_2$(Balb/cJ×129/SvJ)H-2$^d$ rather than Balb/cJ cells. To test this possibility, 2.45×10$^5$ CD4$^+$/CD45RB$^{hi}$ T-cells from Balb/cJ donor mice were injected into C.B-17$^{scid/scid}$ mice. In these animals, skin lesions developed which were similar in nature but appeared less severe than those observed in scid-mice injected with F$_2$(Balb/cJ×129/SvJ)H-2$^d$ donor T-cells.

To compare the skin lesions more objectively, a clinical score was developed which ranged from 0 (no clinical symptoms) to 3 (severely affected animals) (Table 1).

TABLE 1

Criteria of Clinical Score for Mice Injected with Subsets of CD4$^+$ T-Cells.

| Score | Disease Severity | Clinical Findings |
|---|---|---|
| 0 | None | None. |
| 1 | Mild | Erythematous scaling ears. |
| 2 | Moderate | Severe erythema and scaling of ears and/or foot, tail or trunk involvement. |
| 3 | Severe | Extensive erythema and scaling on the trunk, or pustules plus severe erythema and scaling at two or more sites. |

When scid-mice injected with CD4$^+$/CD45RB$^{hi}$ T-cells from F$_2$(Balb/cJ×129/SvJ)H-2$^d$ wild-type mice were evaluated, erythrosquamous skin lesions first were observed 3–4 weeks after injection and 100% of these mice were affected within eight weeks after injection. At twelve weeks after injection, 57% of the recipients had a disease score of 2 indicating moderate disease severity (FIG. 1A). In addition, the average ear thickness in these animals (0.562 mm±0.016 SEM) was increased in comparison with uninjected control animals (0.322±0.009) or CD4$^+$/CD45RB$^{lo}$ cells (0.311±0.006). In contrast, in scid-mice injected with Balb/cJ donor cells, erythrosquamous skin lesions were not seen until 5 weeks after injection. At 12 weeks after injection 71% of these animals were affected, but only 28% developed a clinical score of 2. Thus, the skin disorder affected a smaller proportion of animals, appeared later, and was less severe with Balb/cJ donor cells in comparison to F$_2$(Balb/cJ×129/SvJ)H-2$^d$ donor cells. In each group of recipient mice there were inter-individual differences in the severity of the skin lesions. In addition, in individual mice the severity of the lesions fluctuated somewhat over time.

However, once generated, in the absence of therapy the lesions never completely resolved. The method has reproducibly produced psoriasiform lesions in 100% of animals in 6/6 independent experiments in which animals were injected with $F_2$(Balb/cJ×129/SvJ)H-$2^d$ donor cells.

Scid-mice injected with either Balb/cJ or $F_2$(Balb/cJ×129/SvJ)H-$2^d$ derived CD4$^+$/CD45RB$^{lo}$ T-cells failed to develop either the skin disease or the wasting syndrome. When scid-mice were injected with a mixture of CD4$^+$/CD45RB$^{hi}$ and CD4$^+$/CD45RB$^{lo}$ cells from $F_2$(Balb/cJ×129/SvJ)H-$2^d$ mice, 100% of the animals developed erythrosquamous skin lesions after 12 weeks. However, lesions did not appear until 7 weeks after injection and overall were less severe than in mice injected with CD4$^+$/CD45RB$^{hi}$ cells alone. Similarly, in the group injected with Balb/c derived CD4$^+$/CD45RB$^{hi+lo}$ cells, only 17% (1/6) of the animals developed mild erythrosquamous skin lesions (level 1) and none of the animals developed more severe disease. Taken together, these data suggest that the induction of the murine erythrosquamous skin disorder was due to an immune dysregulation based on a disturbed balance between "pathogenic" (CD4$^+$/CD45RB$^{hi}$) and suppressing (CD4$^+$/CD45RB$^{lo}$) T-cell subpopulations. The increased severity observed when CD4$^+$/CD45RB$^{hi}$ donor cells were derived from $F_2$(Balb/cJ×129/SvJ)H-$2^d$ mice could be due to an increased number of minor histocompatibility antigen mismatches, or to strain-specific differences in the ability of the transferred cells to localize to the skin.

Activated CD4$^+$ T-lymphocytes in the Skin of Mice with Erythrosquamous Skin Lesions To determine if the donor T-cells were present in the skin of mice with erythrosquamous skin lesions, mice were sacrificed at 6, 10, or 12 weeks after injection with CD4$^+$/CD45RB$^{hi}$ T-cells. Immunohistochemical studies revealed abundant CD3$^+$ cells in the dermis of affected areas (412 cells/mm skin, SD=60.2). In addition, a large number of T-cells were observed in the epidermis, primarily in the basal layer but also in suprabasal layers. In contrast, CD3$^+$ lymphocytes were not detected in the skin of CD4$^+$/CD45RB$^{lo}$ injected or in uninjected scid-mice. The same pattern of staining was seen with anti-CD4 mAbs, while positive cells were not detected with anti-CD8α mAbs. Thus, the expression of CD4, but not CD8, was consistent with the phenotype of the injected cells. In contrast, CD45RB, expressed at high levels on the injected cells, was detected on a very small number of the cells within the skin. As CD45RB is thought to be a marker for "naive" T-cells, this observation suggested that the "naive" CD4$^+$/CD45RB$^{hi}$ donor cells had been activated after injection into the recipient mice. In addition, the IL-2 receptor α-chain (CD25) was detected by immunohistochemistry on a subset of both dermal and epidermal lymphocytes (36.5 cells/mm basement membrane, SD=10.95) suggesting activation of these cells. Further evidence for lymphocyte activation and proliferation was obtained using in-vivo labeling with bromo-deoxy-uridine (BrdU), a thymidine analogue. After injection of BrdU, mice were sacrificed and BrdU incorporated into the DNA of proliferating cells was detected in paraffin sections by immunohistochemistry. In skin from CD4$^+$/CD45RB$^{hi}$ injected mice, approximately 5% of the small mononuclear cells in the dermis were stained with anti-BrdU suggesting proliferation.

Activated T-lymphocytes often exert profound effects upon surrounding tissues through the secretion of cytokines. To determine what cytokines were produced in the skin of mice with erythrosquamous lesions, immunohistochemistry was performed. In the skin of uninjected control mice, no expression of IFNγ and weak expression of TNFα was observed in some cells both in the dermis and the epidermis. In contrast, in mice with erythrosquamous skin lesions strong expression of IFNγ was observed in mononuclear cells throughout the dermis and of TNFα diffusely in the dermis and the epidermis. IFNγ and TNFα are known to stimulate the production of other cytokines including IL-1, IL-6, TNFα, and GM-CSF by various cells. In the skin of uninjected control mice, these other cytokines were detected weakly or were undetectable. In contrast, in mice injected with CD4$^+$/CD45RB$^{hi}$ T-cells, IL1α was strongly expressed on some dermal and on all epidermal cells, like TNFα. In addition, IL-6 was expressed strongly by dendritic and mononuclear cells in the dermis and epidermis, suggesting it was produced by cells of macrophage lineage. Finally, expression of GM-CSF was readily detected in the dermis in mononuclear cells, endothelial cells and dendritic cells. Thus, CD4$^+$ T-lymphocytes appeared to produce inflammatory cytokines. In addition, profound expression of cytokines by other cells within the dermis and epidermis was seen.

Epidermal Hyperproliferation and Abnormal Differentiation

After injection with Balb/cJ derived CD4$^+$/CD45RB$^{hi}$ T-lymphocytes the ears of scid-mice were 128% thicker than the ears of uninjected control mice at 12 weeks after injection. Histological examination revealed that the increase in ear thickness was accounted for by a strong acanthosis (increased number of viable cell layers) and hyperkeratosis (increased thickness of the stratum corneum) at least in part. In areas of affected skin, up to 15 layers of epidermal keratinocytes were seen, as opposed to only 2–3 layers in uninjected control mice and in mice injected with CD4$^+$/CD45RB$^{lo}$ T-cells. To determine if the epidermal thickening was due to hyperproliferation or decreased turnover of keratinocytes, BrdU incorporation studies again were used. In mice injected with CD4$^+$/CD45RB$^{hi}$ T-cells, the number of proliferating epidermal cells was increased 20-fold in comparison with uninjected animals (200.13 cells/mm basement membrane, SD=39.89 versus 9.63 cells/mm, SD=1.13). Proliferating cells were found both in the basal layer and in suprabasal layers of the epidermis. In addition, in CD4$^+$/CD45RB$^{hi}$ injected scid-mice the hyperproliferation associated cytokeratin K6 (McGuire, J., et al., (1984), Br. J. Dermatol. 111, 27–37; Sun, T. T., et al., (1983), J. Invest. Dermatol. 81, 109s–115s; Weiss, R. A., et al., (1984), J. Cell Biol. 98, 1397–1406) was strongly expressed throughout the epidermis of the affected skin, but was not detected in interfollicular epidermis of uninjected control mice. Both BrdU staining and cytokeratin K6 reactivity appeared to correlate with the epidermal thickening.

Moreover, within the affected skin focal parakeratosis was seen, further suggesting that the keratinocytes had undergone an abnormal pathway of differentiation. Additional evidence for altered keratinocyte differentiation was obtained by examining expression of differentiation markers. Involucrin is the major precursor protein of the cornified envelope and is a marker for terminal differentiation (Bernard, B. A. et al., (1986), Br. J. Dermatol. 114, 279–283; Dover, R. and Watt, F. M., (1987), J. Invest. Dermatol. 89, 349–352). The integrin α$^6$ chain in association with either β$_1$ (VLA-6) or β$_4$ is a laminin receptor expressed on less differentiated keratinocytes adjacent to the basement membrane in normal mouse skin. As expected, in uninjected control animals, involucrin was faintly stained in a very narrow ribbon within the outermost cell layer and integrin a was expressed by keratinocytes along the basement membrane. In contrast, in the epidermis of CD4$^+$/CD45RB$^{hi}$ T-cell recipients, involucrin was expressed by cells 2–3 cell layers below the granular layer and $\alpha^6$ expression was markedly increased and extended to suprabasal layers. Thus, in mice injected with CD4$^+$/CD45RB$^{hi}$ lymphocytes focal parakeratosis, increased proliferation, and aberrant expression of differentiation associated antigens indicated an alteration of keratinocyte differentiation which is typical for hyperproliferative states.

In inflammatory conditions, MHC class II and leukocyte adhesion molecule expression often are upregulated on cells in response to cytokines such as IFN$\gamma$ and TNF$\alpha$. In the skin of uninjected control scid-mice, MHC class II was expressed by cells with dendritic morphology, while ICAM-1 was expressed by some endothelial cells. In contrast, in the skin of mice injected with CD4$^+$/CD45RB$^{hi}$ T-cells strong expression of MHC class II was seen on cells within the dermis and de-novo expression on keratinocytes from the basal layer up to the upper spinous layers. Moreover, expression of ICAM-1 was dramatically increased in the dermis, due to an increased number of blood vessels at least in part (see below). ICAM-1 also was expressed de-novo by keratinocytes in the basal and in the first one or two suprabasal layers. These observations suggest that alterations have occurred in the expression of molecules important in interactions with leukocytes on skin epidermal and endothelial cells.

Dermal Angiogenesis in CD4$^+$/CD45RB$^{hi}$ Injected Scid-Mice

The dermal blood vessels appeared to be increased in number and size when mice injected with CD4$^+$/CD45RB$^{hi}$ lymphocytes were compared with mice injected with CD4$^+$/CD45RB$^{lo}$ cells and with uninjected mice. To confirm this observation, immunohistochemical analyses were performed using an anti-CD31 mAb. CD31 (PECAM-1, platelet-endothelial cell adhesion molecule) is an endothelial cell junction molecule which also mediates interactions of endothelial cells with leukocytes and platelets. This molecule is expressed constitutively on endothelial cells and has proven to be a reliable marker of blood vessels, "particularly in the setting of angiogenesis" (DeLisser, H. M., et al., (1994), Immunol. Today 15, 490–495). Anti-CD31 staining revealed a strong increase in the number and size of dermal blood vessels in CD4$^+$/CD45RB$^{hi}$ injected mice, relative to control mice. Vascular endothelial growth factor/vascular permeability factor (VEGF, VPF) is a potent angiogenesis factor (Detmar, M., et al., (1995), J. Invest. Dermatol. 105, 44–50; Keck, P. J., et al., (1989), Science 246, 1309; Leung, D. W., et al., (1989), Science 246, 1306–1309; Senger, D. R., et al., (1983), Science 219, 983–985) which is overexpressed in psoriatic skin lesions (Detmar, M., et al., (1994), J. Exp. Med. 180, 1141–1146). To determine if VEGF expression was increased in the CD4$^+$/CD45RB$^{hi}$ injected mice, in-situ hybridization was performed using a VEGF-riboprobe. While VEGF mRNA was barely detectable in the epidermis of control mice, it was detected strongly in the epidermis of CD4$^+$/CD45RB$^{hi}$ injected mice. Likewise, the flt-1 and flk-1 high affinity VEGF receptors (Finnerty, H., et al., (1993), Oncogene 8, 2293–2298; Matthews, W., et al., (1991), Proc. Natl. Acad. Sci. USA 88, 9026–9030) were expressed more strongly by the dermal endothelial cells of mice injected with CD4$^+$/CD45RB$^{hi}$ T-cells, similar to what is observed in human psoriatic skin lesions (Detmar, M., et al., (1994), J. Exp. Med. 180, 1141–1146). Thus, it appears that increased levels of VEGF expression within the hyperproliferative epidermis and increased expression of VEGF receptors by endothelial cells both contribute to the angiogenesis observed within the psoriasiform skin lesions.

Localization of Neutrophils and Mast Cells to the Skin

Abundant polymorphonuclear cells and mast cells were observed within the dermis in hematoxylin and eosin (H&E) stained skin sections from mice injected with CD4$^+$/CD45RB$^{hi}$ T-lymphocytes. Moreover, neutrophils were seen in focal aggregates and in subcorneal microabscesses within the epidermis. In contrast, only a few mast cells and no neutrophils were visible in the skin of control mice. To evaluate this leukocytic infiltrate further, neutrophils and mast cells were visualized by chloroacetate-esterase staining (Yam, L. T., et al., (1971), Am. J. Clin. Pathol. 55, 283–290). In this analysis, neutrophils were seen within the vasculature adjacent to endothelial cells, in the perivascular area, and diffusely within the dermis. In addition, neutrophils were seen in focal aggregates and in microabscesses within the epidermis and in microabscesses within sloughed stratum corneum. Similar results were obtained with cryostat-cut sections stained for integrin $\alpha^M$. The expression of ICAM-1 by endothelial cells and keratinocytes and of the $\alpha^M\beta_2$ integrin (Mac-1) by neutrophils adjacent to endothelial cells within the blood vessels and in the epidermis suggests that ICAM-1/$\alpha^M\beta_2$ may participate in the apparent extravasation and migration of neutrophils in this system. While a few mast cells were present in the dermis of control animals, the number of cutaneous mast cells was dramatically increased in the dermis of CD4$^+$/CD45RB$^{hi}$ injected mice. In these mice, approximately 5% of the mast cells were surrounded by extracellular granules which were not seen in the dermis of control mice and suggested activation. Thus, in CD4$^+$/CD45RB$^{hi}$ injected mice both the location and type of inflammatory cells infiltrating the skin were similar to those seen in human psoriatic lesions.

B. Discussion

Overall, the clinical and histopathological findings observed in the skin of scid-mice injected with CD4$^+$/CD45RB$^{hi}$ T-lymphocytes closely resembled those seen in human psoriasis. Like in psoriatic skin (Christophers, E., and Sterry, W. (1993). Psoriasis. In Dermatology in General Medicine, T. B. Fitzpatrick, A. Z. Eisen, K. Wolff, I. M. Freedberg and K. F. Austen, eds. (New York: McGraw-Hill, Inc.), pp. 489–514), keratinocyte hyperproliferation, changes in epidermal differentiation markers, and increased expression of MHC class II and ICAM-1 were observed in the skin lesions of these animals. Moreover, the prominent dermal angiogenesis and dilation of blood vessels characteristically seen in human psoriasis were observed in the injected mice. The dermis and the epidermis of injected mice were densely infiltrated with T-lymphocytes, mast cells were concentrated below the epidermis, and neutrophils infiltrated the dermis and formed microabscesses within the epidermis. Finally, striking parallels were observed in the cytokine expression pattern reported in the skin of patients with psoriasis and in the injected mice. As in human psoriatic skin, the production of inflammatory cytokines including IFN$\gamma$ and TNF$\alpha$, as well as IL-1, VEGF, GM-CSF, and IL-6 appeared to be increased dramatically in injected animals in comparison with uninjected mice. Thus, the abnormalities in human psoriasis are substantially the same as those observed in the skin of scid mice injected with CD4$^+$/CD45RB$^{hi}$ lymphocytes. Thus, this is the first experimental system known to model the immuno-pathogenesis of psoriasis, to be inducible in one to two months in virtually all recipient animals and which does not require the use of human skin for model generation.

C. Experimental procedures

Animals

C.B-17$^{scid/scid}$ were purchased from Taconic Farms (Germantown, N.Y.). Balb/c and 129/SvJ mice were obtained from the Jackson Laboratory (Bar Harbor, Me.). All animals were maintained in the animal care facility of Harvard Medical School in specific pathogen-free conditions in microisolator cages. They received autoclaved food and water. Only female mice were used as recipients and donors in these studies. Recipient scid-mice were 5–8 weeks of age when used and the average age of donor mice was 14–15 weeks.

Antibodies

The following mAbs were used as isotype matched negative controls in immunohistochemistry: rat IgG1 (R59-40; Pharmingen, San Diego, Calif.), rat IgG2a (R35-95; Pharmingen), rat IgG2b (SFR3-DR5, anti-human HLA-DR5; ATCC, Rockville, Md.), and hamster IgG (UC8-4B3, anti-trinitrophenol; Pharmingen). When polyclonal rabbit sera were used, normal rabbit serum served as control. The following mAbs were used to detect murine antigens: anti-CD3∈ (500A2, hamster IgG, Pharmingen), anti-CD4 (RM4-5, rat IgG2a, Pharmingen), anti-CD8α (53-6.72, rat IgG2a, ATCC), anti-CD45RB (MB23G2, rat IgG2a, ATCC and 16A, FITC-conjugated rat IgG2a, Pharmingen), anti-Cd25 (high affinity IL-2 receptor α-chain, 3C7, rat IgG2b, Pharmingen), anti-CD11b ($\alpha^M$-integrin, Mac-1, M1/70, rat IgG2b, ATCC), anti-CD 18 ($\beta_2$-integrin, 2E6, hamster IgG, ATCC), anti-B220 (RA3-6B2, rat IgG2a, Pharmingen), anti-MHC class II (I-A antigens, M5/114.15.2, rat IgG2b, ATCC), anti-human involucrin (SY5, mouse IgG, Santa Cruz), anti-CD49f ($\alpha^6$ integrin, GoH3, rat IgG, Dianova, Hamburg, Germany), anti-MHC class II (N22, hamster IgG, ATCC), anti-CD54 (ICAM-1, YN1/1.7.4, rat IgG2a, ATCC), anti-CD106 (VCAM-1, M/K-2.7, rat IgG1, ATCC), anti-CD31 (PECAM-1, MEC13.3, rat IgG2a, Pharmingen), anti-IFNγ (XMG1.2, rat IgG1, Phaimingen), anti-IL-6 (MP5-20F3, rat IgG1, Pharmingen), anti-GM-CSF (MP1-22E9, rat IgG2a, Pharmingen), anti-CD32/CD16 (Fc-γII/III receptor, 2.4G2, rat IgG2b, ATCC), anti-H-2D$^d$ (34-2-12, biotinylated C3H IgG2a, Pharmingen), anti-H-2K$^b$ (AF6-88.5, biotinylated Balb/c IgG2a, Pharmingen). Rabbit sera against murine keratin 6 (Roop, D. R., et al., (1984), J. Biol. Chem. 259, 8037–8040; Roop, D. R., et al., (1985), Ann. N. Y. Acad. Sci. 455, 426–435), TNFα (#IP-400, Genzyme, Cambridge, Mass.) and IL- 1α (#IP-110, Genzyme) also were used. Biotinylated goat-anti-hamster serum and mouse adsorbed rabbit-anti-rat serum were purchased from Vector Laboratories Inc. (Burlingame, Calif.) and goat-anti-rat IgG MicroBeads were obtained from Miltenyi Biotec Inc. (Auburn, Calif.).

H-2 Typing $F_2$ (Balb/cJ×129/SvJ) donor mice were tail bled and peripheral blood mononuclear cells (PBMC) were isolated by density gradient centrifugation using Histopaque-1083 (Sigma Chemicals, St. Louis, Mo.). T he PBMC were incubated with 10 μg/ml anti-FcγRII/III for 10 min. An aliquot of the PBMC from each mouse then was incubated for 30 min with 10 μg/ml of either biotinylated anti-H-2 D$^d$ (mAb 34-2-12), anti-H-2K$^b$ (mAb AF6-88.5), or staining buffer, washed and then incubated with a 1:100 dilution of PE-Streptavidin (Pharmingen), washed and analyzed in a FACSort (Becton Dickinson). Animals which expressed at least one H-2$^d$ allele were designated H-2$^d$ and utilized in the analysis.

Cell Purification and Reconstitution of Scid-Mice

CD4$^+$/CD45RB$^{hi}$ and CD4$^+$/CD45RB$^{lo}$ T-cells were purified from spleens of Balb/c or $F_2$(Balb/cJ×129/SvJ)H-2$^d$ mice as described by Powrie et al. (Morrissey, P. J., et al., (1993), J. Exp. Med. 178, 237–244; Morrissey, P. J., et al., (1995), J. Immunol. 154, 2678–2686; Powrie, F., et al., (1994), J. Exp. Med. 179, 589–600; Powrie, F., et al., (1993), Int.1 Immunol. 5, 1461–1471) with modifications as described herein. Briefly, spleens from 4–6 donor mice were removed, a single cell suspension was prepared and erythrocytes were lysed by incubation in 0.17M NH$_4$Cl for 10 minutes. The cell suspension then was incubated for 15 minutes with 20 μg/10$^7$ cells each of azide-free anti-B220 (mAb RA3-6B2), anti-integrin $\alpha^M$ (mAb M1/70), anti-CD8α(mAb 53-6.72) and anti-I-A$^{b,d,q}$ (mAb M5/114.15.2), washed twice with 5% FCS in PBS (MACS-buffer), then incubated with 20 μl goat-anti-rat IgG microbeads (Miltenyi Biotec Inc., Auburn, Calif.) per 10$^7$ cells for 15 min, and washed again. Cells which did not bind to a MACS separation column (type CS, Miltenyi Biotec Inc.) were collected. The enriched CD4$^+$ population (>85% CD4$^+$) was incubated with 15 μl PE-conjugated anti-CD4 (mAb RM4-5) per 10$^7$ cells and 25 μl FITC-conjugated anti-CD45RB (mAb 16A) per 10$^7$ cells for 30 min, washed and sorted using a FACS Vantage (Becton Dickinson, San Jose, Calif.). From the CD4$^+$ population, the 35–40% of cells stained most brightly with anti-CD45RB and the 15–20% of least bright stained cells were selected as CD45RB$^{hi}$ and CD45RB$^{lo}$, respectively. Each of the collected cell populations was >93% pure. Each recipient scid-mouse was intraveneously injected with either 2.45×10$^5$ CD4$^+$/CD45RB$^{hi}$ cells, 2.45×10$^5$ CD4$^+$/CD45RB$^{lo}$ cells, or a mixture of 2.45×10$^5$ CD4$^+$/CD45RB$^{hi}$ and 0.8×10$^5$ CD4$^+$/CD45RB$^{lo}$ cells in 300 μl PBS. All purification steps were carried out under sterile conditions at 4° C. or on ice. In order to remove sodium azide, MicroBeads were pre-run over a separation column and washed twice with MACS buffer.

Clinical Evaluation

Mice were weighed and evaluated clinically at weekly intervals. To more objectively assess the disease development, a clinical score was developed (Table 1, above). The ear thickness was determined using a skin thickness gage ("Oditest" from Dyer Inc., Lancaster, Pa. or Fisher Scientific, Pittsburgh, Pa.).

Histochemistry Immunohistochemistry and BrdU-Labeling

Histological procedures were performed using plastic-embcdded tissue. Briefly, tissue samples were fixed in 4% paraformaldehyde at 4° C. overnight and dehydrated 30 min each in 70%, 90%, and 2×30 min in 100% acetone. The samples then were infiltrated and embedded in JB-4 resin according to the manufacturer's instructions (Polysciences Inc., Warrington, Pa). 1 μm sections were stained with hematoxylin and eosin according to standard protocols. Chloroacetate-esterase staining was performed as described previously (Yam, L. T., et al., (1971), Am. J. Clin. Pathol. 55, 283–290). Briefly, prior to each staining new fuchsin solution was prepared by dissolving 1 g new fuchsin (Sigma Inc., St. Louis, Mo.) in 25 ml 2N HCl and adding an equal volume of freshly prepared 4% NaNO$_2$. Then, 0.05 ml of the new fuchsin solution and 1 mg naphthol-AS-D-cloroacetate (Sigma) dissolved in 0.5 ml N,N'-dimethyl-formamide (Sigma) were added to 9.5 ml phosphate buffer (0.15M, pH 7.6). Tissue sections were incubated with the final solution for 10 min at room temperature, rinsed four times with water, counterstained for 2 minutes with 1% methyl green (in 0.1N sodium acetate, pH 4.2), rinsed with water, and mounted.

For immunohistochemistry, tissue samples were embedded in O.C.T. compound (Miles Inc., Elkhart, Ind.), snap frozen in liquid nitrogen and stored at −20° C. 5 μm cryostat-cut sections were stained by the ABC-immunoperoxidase method (Vector). Briefly, sections were air dried for 30 min, fixed in acetone for 10 min at room temperature, and incubated with buffer containing 30% bovine calf serum, 10% normal goat serum, 5% normal rabbit serum, and 1% normal horse serum for 30 min. Unless otherwise stated, sections then were incubated with 10 μg/ml of the primary antibody for 1 h. After washing with PBS, endogeneous peroxidase was blocked with 0.3% H202 in PBS for 20 min. Slides were submerged three times for 3 min in PBS and then incubated with biotinylated goat-anti-hamster, mouse adsorbed rabbit-anti-rat, or horse-anti-mouse serum (Vector), according to the primary antibody used. After washing, sections were incubated with the avidin-peroxidase complex according to the manufacturer's instructions (Vector) for 45 min, washed with PBS, and submerged in 3-amino-9-cthylcarbazole (red reaction product) or diaminobenzidine (brown reaction product) (both from Sigma) substrate solution in 0.1M acetate buffer (pH 5.2). Color development was monitored by microscopy, and the reaction stopped by placing the slides in 10% formalin in acetate buffer (pH 5.2) for 10 min. Subsequently, slides were counterstained with hematoxylin, extensively washed with water, incubated 3 min in a saturated solution of $LiCO_3$, washed, and mounted with Gel/Mount (Biomeda Corp., Foster City, Calif.). All steps were carried out at room temperature.

In order to detect proliferating cells, 3 uninjected mice and 3 mice injected with $CD4^+/CD45RB^{hi}$ T-cells were injected intraperitoneally with 5 mg BrdU in 500 μl PBS at both 9 and 6 h prior to sacrifice. 4 μm paraffin-sections were immersed in 0.03% H202 in methanol for 30 min and washed with TBS. Sections were denatured by incubation with 0.4% pepsin (Sigma) in 0.1N HCl for 20 min at 37° C. and then 0.8N HCl for 20 min at room temperature. Sections then were stained by the ABC-immunoperoxidase method (Vector) as described above using an anti-BrdU mAb (Becton Dickinson).

In-situ Hybridization

5 μm cryostat-cut sections of frozen tissue were mounted on slides pretreated with 3-aminopropylethoxysilane (Digene Inc., Beltsville, Md.). Polymerase chain reaction (PCR) was used to prepare a 393 bp partial rat VEGF cDNA as described (Leung, D. W., et al., (1989), Science 246, 1306–1309), except that a different antisense primer (CCGGAAT TCAGCGCCTCGGCTTGTC) (Seq. I.D. No. 1) was used. After confirming the identity of the CDNA clone, it was subcloned into pGEM-3Zf(+) (Promega, Madison, Wis.). Single stranded RNA probes were synthesized which react with all known VEGF isoforms using a Riboprobe Gemini II kit (Promega) in the presence of $\alpha$-$^{35}$[S] UTP. To prepare the murine flk-1 transcription template, a 392 bp fragment encompassing nucleotides 268–660 of the previously described sequence (Matthews, W., et al., (1991), Proc. Natl. Acad. Sci. USA 88, 9026–9030) was cloned into pGEM-T (Promega). To prepare murine flt-1 templates, a 640 bp CDNA fragment encoding from amino acids 832–1045 (Finnerty, H., et al., (1993), Oncogene 8, 2293–2298) was obtained using degenerate PCR and was cloned into pBluescript II KS+ (Stratagene, La Jolla, Calif.) for linearization and transcription of riboprobes. For all three mRNAs, antisense and control sense probes were evaluated on sequential tissue sections as described previously (Brown, L. F., et al., (1995), J. Invest. Dermatol. 104, 744–749) under RNAse free conditions. Briefly, slides were hybridized overnight at 50° C. with $^{35}$S-methionine labeled riboprobes in buffer containing 0.3M NaCl, 0.01M Tris (pH 7.6), 5 mM EDTA, 0.02% Ficoll, 0.02% polyvinylpyrrolidone, 0.02% BSA, 50% formamide, 10% dextran sulfate, 0.1 mg/ml yeast tRNA, and 0.01M dithiothreitol. Slides then were washed, dehydrated, and dried as described (Brown, L. F., et al., (1995), J. Invest. Dermatol. 104, 744–749) and, subsequently, coated with Kodak NTB 2 emulsion and stored in the dark for 2 weeks. The emulsion was developed with Kodak D19 developer and the slides were counterstained with hematoxylin (Fisher). Signals were visualized as bright blue dots by darkfield microscopy.

Example 2

$\alpha^E$ deficient Splenocvtes as Donor Lymphocytes.

A. Construction of a Mouse Containing a Mutated $\alpha^E$ Gene

Figure 2:
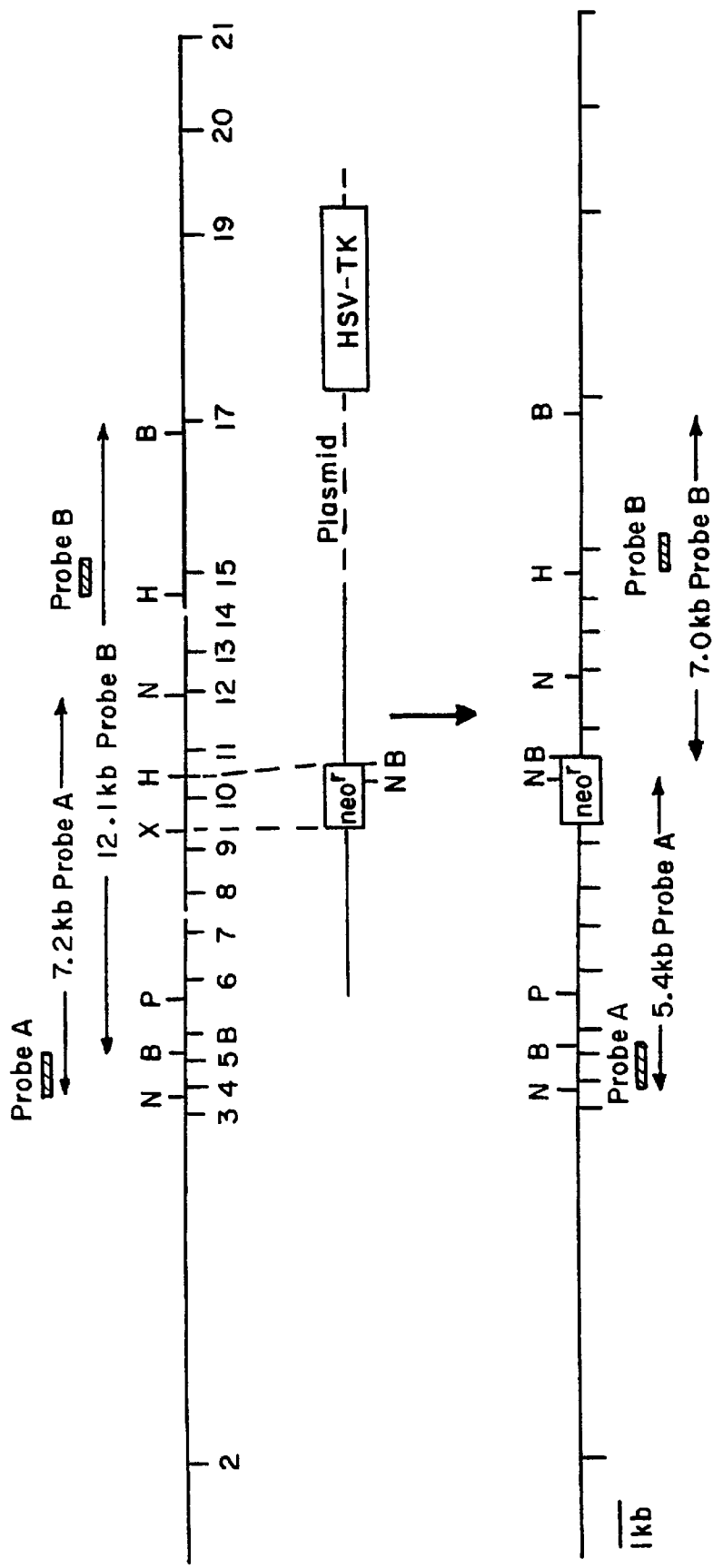
FIG. 2: A schematic representation of the construct for disrupting the $\alpha^E$ encoding gene

In order to produce a mouse in which the $\alpha^E$ encoding gene had been disrupted by homologous recombination, a construct was generated, and a strategy was devised to identify the resulting clones which had integrated the construct into the $\alpha^E$ encoding gene (FIG. 2). The restriction endonuclease sites used to prepare the construct, and to analyze the clones and mice are N=Nco I, B=Bam HI, P=Pst I, X=Xho I, H=Hind III. The wild-type $\alpha^E$ encoding gene is represented by the upper schematic, the $\alpha^E$ targeting construct is represented by the middle schematic and the disrupted $\alpha^E$ allele is represented by the lower schematic.

The construct was transfected by electroporation into the embryonic stem (ES) cell line D3. The transfected ES cell line was selected for G418 resistance and then cloned by limiting dilution. Restriction endonuclease digestion followed by Southern blot analysis of genomic DNA was used to identify clones in which homologous recombination had occured. Specifically, the shorter Nco I and Bam HI restriction endonuclease fragments were detected by Probe A and Probe B in cells which contained a disrupted allele.

Two of the clones which integrated the $\alpha^E$ construct into the genome by homologous recombination were injected into Balb/c blastocysts. These blastocytes then were implanted into Balb/c female mice to produce chimeric animals. The chimeric animals were bred, and the F1 animals analyzed by Southern blot analysis of tail genomic DNA to identify mice which transmitted the disrupted $\alpha^E$ gene to the offspring. The heteroxygous animals were mated to yield (129/SvxBal b/c) F2 animals, some of which are homozygous for the disrupted a $\alpha^E$ gene ($\alpha^E$/null) and lack $\alpha^E$ protein expression.

B. Isolation of $\alpha^E$ Deficient Splenocytes

The spleen was removed and a single cell suspension prepared by mechanical disruption. The splenocytes were spun down at 1200 rpm for 5 minutes and resuspended in 0.17M ammonium chloride solution for 10 minutes on ice. The cell suspension was diluted gradually 1:5 or 1:10 in cold DMEM media (Dulbecco's modified essential media), spun and washed with 10 ml of cold DMEM. The cells were resuspended in 10 ml of DMEM and passed over a sterile glass wool column (approximately 300 mg of glass wool compressed to 1.5 ml in a 10 ml syringe which had been preincubated with DMEM media). The cells which passed through the column were washed.

C. Administration of $\alpha^E$ Deficient Splenocytes or Wild-Type Splenocytes to a Recipient Mouse and Clinical Assessment of Recipient Animals $1.7 \times 10^7$ cells (unfractionated splenocytes from $\alpha^E$/null animals) in 300 μl of PBS was injected into each recipient mouse. In these animals, erythema of the ears without flaking developed. In histopathologic evaluation, cutaneous infiltration of T lymphocytes was associated with epidermal thickening (acanthosis), neutrophil infiltration, and microabscess formation, as well as an increase in the number and size of blood vessels. The mean ear thickness of the $\alpha^E$ deficient splenocyte recipient mice (0.438 mm±0.023 SEM, n=3) was greater than in uninjected control mice (0.248±0.007, n=3) or in wild-type recipients (0.307±0.031, n=3).

Example 3
Protocol for Testing the Efficacy of a Therapeutic Agent for Treating An Inflammatory Skin Condition
A. Preparation of Animal Model Wild-type CD4$^+$/CD45RB$^{hi}$ cells derived from F$_2$(Balb/cJ×129/SvJ)H-2$^d$ donors were transferred into C.B-17$^{scid/scid}$ recipients. 2.5×10$^5$ donor cells were administered in accordance with the above-described procedures (See, e.g., Example 1).

B. Administration of a Therapeutic Agent

Figure 3A:
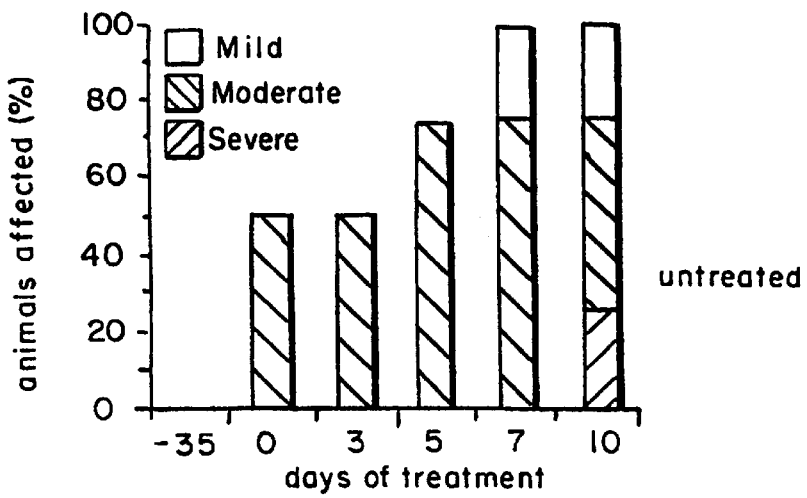
FIGS. 3A–3C: Effect of administration of no treatment ("untreated", FIG. 3A), cyclosporine (FIG. 3B), and UV-B (FIG. 3C) on the overall severity of the disease.
Figure 3B:
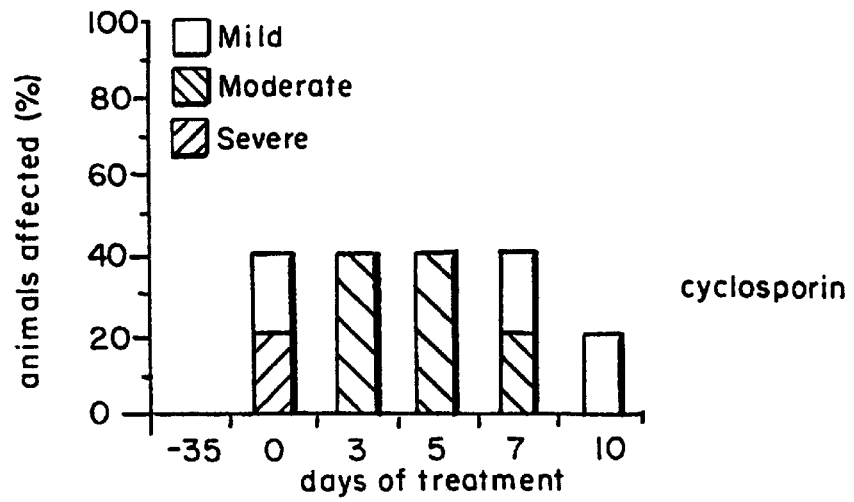
Figure 3C:
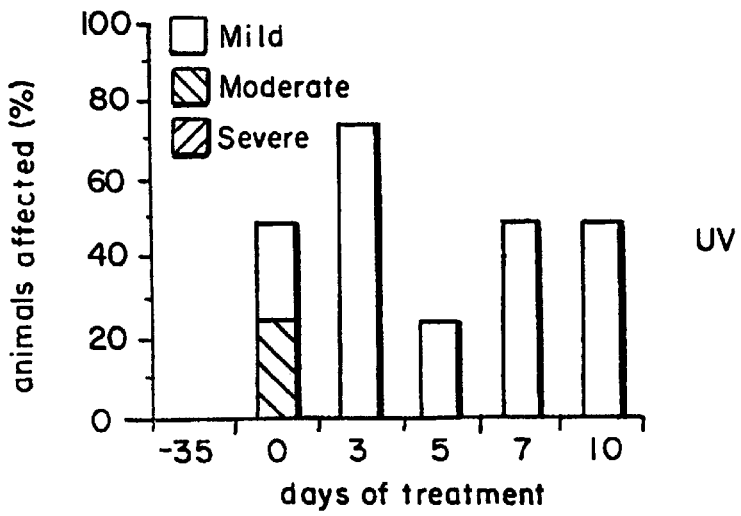

Two therapeutic agents, ultraviolet light irradiation and cyclosporine (Sandimmune®, cyclosporine concentrate for injection, USP; Sandoz, East Hanover, N.J.), were separately tested for efficacy in the animal model disclosed herein. For UV treatment, 0.04 mJoules/cm$^2$ of 310 nm UV-B was administered to the surface of the animal. 30 mg/kg/dose of cyclosporin A was administered intraperitoneally. Each treatment was administered on Monday, Wednesday, and Friday, beginning 5 weeks after injection of the donor cells to generate the model. The clinical score of the animals was determined at the time indicated after initiation of treatment. The overall height of the bar reflects the percent of animals with clinical signs of the psoriasiform disorder (FIG. 3). The texture of the bar indicates the overall severity. The open portion of the bar indicate animals with mild disease (score=1), cross hatched bars indicate moderate severity (score=2), speckled bars indicate severe disease (score=3).

The ear thickness (measured using a Dyer skin thickness gage) was determined in each animal 10 days after initiating therapy. This analysis showed a statistically significant difference in the mean ear thickness when untreated animal models (0.568 mm±0.044 SEM) were compared to animal models which received cyclosporine treatment (0.345 mm±0.045) or UV-B irradiation (0.375 mm±0.046) (n=4 for all groups except cyclosporine, n=5 for cyclosporine).

Each of the above-identified references, patents/patent publications is incorporated in its entirety herein by reference. The preceding is merely a detailed description of certain preferred embodiments. It therefore should be apparent to those skilled in the art that various modifications and equivalents can be made without departing from the spirit or scope of the invention.

A sequence listing is presented below and is followed by what is claimed:

We claim:

1. A method of preparing a mouse model of an inflammatory skin condition, comprising:

(1) administering to a recipient mouse a sufficient number of donor lymphocytes to mediate the inflammatory skin condition, wherein the recipient mouse is immune system deficient and lacks functional T cells;

wherein the donor lymphocytes are matched to one or both alleles of the major histocompatibility complex of the recipient mouse and are selected from the group consisting of: $\alpha^E$ deficient splenocytes, $\alpha^E$ deficient naive CD4$^+$ T-lymphocytes, $\alpha^E$ deficient CD4$^+$/CD45RB$^{hi}$ T-lymphocytes, $\alpha^E$ deficient naive CD8$^+$ T-lymphocytes, naive CD4$^+$ T-lymphocytes, naive CD8$^+$ T-lymphocytes, naive CD4$^-$/CD8$^-$ T-lymphocytes, $\alpha^E$ deficient naive CD4$^-$/CD8$^-$ T-lymphocytes and $\alpha^E$ wild-type CD4$^+$ /CD45RB$^{hi}$ T-lymphocytes, wherein administering the lymphocytes comprises a method selected from the group consisting of intravenous injection, retro-orbital injection, intra-arterial injection, intra-peritoneal injection and subcutaneous injection, wherein the sufficient number of donor lymphocytes is between about $1\times10^3$ and about $1\times10^8$ cells and is sufficient to induce in each recipient mouse, within about 70 days following administration of the donor lymphocytes to the recipient mouse, at least 75% of the symptoms selected from the group consisting of: (1) erythematous skin with loose whitish scales; (2) acanthosis, hyperkeratosis and focal parakeratosis; (3) keratinocyte hyper proliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis; and (2) allowing the inflammatory skin condition to develop.

2. A mouse model of inflammatory skin disease, comprising:

an immune system deficient recipient mouse that has been reconstituted with donor lymphocytes, wherein the donor lymphocytes are matched to one or both alleles of the major histocompatibility complex of the recipient mouse, and wherein the recipient mouse is immune system deficient and lacks functional T cells and wherein each recipient mouse exhibits, within 70 days following administration of the donor lymphocytes, cutaneous T-lymphocyte infiltration and at least 75% of the symptoms selected from the group consisting of: (1) erythematous skin with loose whitish scales; (2) acanthosis, hyperkeratosis and focal parakeratosis; (3) keratinocyte hyperproliferation; (4) changes in keratinocayte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis.

3. A composition comprising:

donor lymphocytes contained in a container, wherein the container contains a single dose of donor lymphocytes that are $\alpha^E$ deficient for administration to a recipient mouse that is immune system deficient and that lacks functional T cells, wherein the donor lumphocytes are matched to one or both alleles of the major histocompatibility complex of the recipient mouse and wherein the single dose of donor lymphocytes is sufficient to induce in the recipient mouse, within 70 days following administration, cutaneous T-lymphocyte infiltration and at least 75% of the symptoms selected from the group consisting of: (1) erythematous skin with loose whitish scales; (2) acanthosis, hyperkeratosis and focal parakeratosis; (3) keratinocyte hyperproliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis.

4. The method of claim 1, wherein the inflammatory skin condition is selected from the group consisting of psoriasis, eczema, para-psoriasis associated with immune deficiency, and cutaneous T-cell lymphoma.

5. The method of claim 1, wherein the sufficient number of donor lymphocytes is the number of donor lymphocytes that is sufficient to induce in each recipient mouse a condition in which both the location and type of inflainmmatory cells infiltrating the skin are substantially the same as the location and type of inflammatory cells infiltrating the skin in human psoriatic lesions.

6. The method of claim 1, wherein the sufficient number of donor lymphocytes is the number of donor lymphocytes that is sufficient to induce in each recipient mouse, within about 70 days following administration of the donor lymphocytes to the recipient mouse, cutaneous T-lymphocyte infiltration.

7. The method of claim 6, wherein the changes in cytokine expression patterns are changes in the expression of cytokines selected from the group consisting of gamma-interferon, IL-1α, GM-CSF, TNF-alpha, IL-2, IL-6, IL-8 and VEGF/VPF.

8. The method of claim 7, wherein the number of donor lymphocytes is sufficient to induce in each recipient mouse at least 75% of the symptoms within 35 days following administration of the donor lymphocytes to the recipient mouse.

9. The method of claim 1, wherein the donor lymphocytes are selected from the group consisting of $\alpha^E$ deficient splenocytes and $\alpha^E$ deficient naive CD4+ T-lymphocytes.

10. A method of testing the efficacy of a therapeutic agent for treating an inflammatory skin condition, comprising:

(a) evaluating the symptoms of the inflammatory skin condition in at least one mouse model of inflammatory skin disease, said mouse model comprising:

an immune system deficient recipient mouse that has been reconstituted with donor lymphocytes, wherein the donor lymphocytes are matched to one or both alleles of the major histocompatibility complex of the recipient mouse, and wherein the recipient mouse is immune system deficient and lacks functional T cells and wherein each recipient mouse exhibits, within 70 days following administration of the donor lymphocytes, cutaneous T-lymphocyte infiltration and at least 75% of the symptoms selected from the group consisting of: (1) erythematous skin with loose whitish scales; (2) acanthosis, hyperkeratosis and focal parakeratosis; (3) keratinocyte hyperproliferation; (4) changes in keratinocyte differentiation; (5) increased expression of MHC class II in one or more skin lesions: (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine patterns observed in the skin of human patients with psoriasis;

(b) contacting the at least one mouse model with the therapeutic agent; and (c) reevaluating the symptoms of the inflammatory skin condition in the at least one mouse model, wherein prevention, delayed onset or reduction of one or more of the symptoms in the at least one mouse model indicates that the therapeutic agent is efficacious for treating the inflammatory skin condition.

11. A method of testing the efficacy of a therapeutic agent for treating an inflammatory skin condition, comprising:
(1) evaluating the symptoms of the inflammatory skin condition in at least one mouse model produced by the method of claim 1;
(2) contacting the at least one mouse model with the therapeutic agent; and
(3) reevaluating the symptoms of the inflammatory skin condition in the at least one mouse model, wherein prevention, delayed onset or reduction of one or more of the symptoms in the at least one mouse model indicates that the therapeutic agent is efficacious for treating the inflammatory skin condition.

12. The method of claim 11, wherein the therapeutic agent is selected from the group consisting of immunosuppressive agents, cytostatic agents, retinoids, tar and related compounds, anthralines, vitamin D3 analogues, ultraviolet irradiation, ultraviolet irradiation with a photosensitizing agent, agents which modulate cytokine functional activity and adhesion molecules.

13. A mouse model of an inflammatory skin condition, wherein the mouse model is produced by the process of claim 1, wherein the mouse model develops said inflammatory skin condition.

14. The mouse model of claim 2, wherein the mouse model is not a transgenic mouse and does not comprise human skin.

15. The composition of claim 3, wherein the donor lymphocytes are selected from the group consisting of: $\alpha^E$ deficient splenocytes, $\alpha^E$ deficient naive CD4$^+$ T-lymphocytes, $\alpha^E$ deficient CD4$^+$/CD45RB$^{hi}$ T-lymphocytes, $\alpha^E$ deficient naive CD8$^+$ T-lymphocytes, and $\alpha^E$ deficient naive CD4$^-$/CD8$^-$ T-lymphocytes.

16. The composition of claim 3, wherein the single dose comprises between about $1\times10^3$ and about $1\times10^8$ cells.

17. A method of preparing a mouse model of an inflammatory skin condition, comprising:
(1) intravenously administering to a recipient mouse from the C.B-17/Tac-scidDF$^{scid/scid}$ lineage about $2.5\times10^5$ of donor lymphocytes that are CD4$^+$/CD45RB$^{high}$ T cells derived from F$_2$ progeny of BALB/cJ×129/SvJ donor mice expressing the H-2$^d$ MHC haplotype; and
(2) allowing the inflammatory skin condition to develop, wherein the inflammatory skin condition is psoriasis or psoriasis associated with immune deficiency.

18. A method of preparing a mouse model of an inflammatory skin condition, comprising:
(1) intravenously administering to a recipient mouse from the C.B-17/Tac-scidDF$^{scid/scid}$ lineage about $2.5\times10^5$ of donor lymphocytes that are CD4$^+$/CD45RB$^{high}$ T cells derived from F$_2$ progeny of BALB/cJ×129/SvJ donor mice expressing the H-2$^d$ MHC haplotype; and
(2) allowing the inflammatory skin condition to develop, wherein the inflammatory skin condition develops within about 70 days following administration of the donor lymphocytes to the recipient mouse, and wherein the inflammatory skin condition exhibits at least 75 percent of the symptoms selected from the group consisting of: (1) erythematous skin with loose whitish scales; (2) acanthosis, hyperkeratosis and focal parakeratosis; (3) keratinocyte hyper proliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis.

19. A method of preparing a mouse model of an inflammatory skin condition, comprising:
(1) administering to a recipient mouse from the C.B-17/Tac-scidDF$^{scid/scid}$ lineage about $2.5\times10^5$ of donor lymphocytes that are CD4$^+$/CD45RB$^{high}$ T cells derived from F$_2$ progeny of BALB/cJ×129/SvJ donor mice expressing the H-2$^d$ MHC haplotype; and
(2) allowing the inflammatory skin condition to develop, wherein the inflammatory skin condition is psoriasis or psoriasis associated with immune deficiency,
wherein administering the lymphocytes comprises a method selected from the group consisting of intravenous injection, retro-orbital injection, intra-arterial injection, intra-peritoneal injection and subcutaneous injection.

20. A method of preparing a mouse model of an inflammatory skin condition, comprising:
(1) intravenously administering to a recipient mouse from the C.B-17/Tac-scidDF$^{scid/scid}$ lineage a sufficient number of donor lymphocytes that are CD4$^+$/CD45RB$^{high1328}$ T cells derived from F$_2$ progeny of BALB/cJ×129/SvJ donor mice expressing the H-2$^d$ MHC haplotype; and
(2) allowing the inflammatory skin condition to develop, wherein the inflammatory skin condition is psoriasis or psoriasis associated with immune deficiency,
wherein the sufficient number of donor lymphocytes is between about $1\times10^3$ and about $1\times10^8$ cells.

21. A method of preparing a mouse model of an inflammatory skin condition, comprising:
(1) administering to a recipient mouse from the C.B-17/Tac-scidDF$^{scid/scid}$ lineage a sufficient number of donor lymphocytes that are CD4$^+$/CD45RB$^{high}$ T cells derived from BALB/cJ donor mice or F$_2$ progeny of BALB/cJ×129/SvJ donor mice expressing the H-2$^d$ MHC haplotype,
wherein administering the lymphocytes comprises a method selected from the group consisting of intravenous injection, retro-orbital injection, intra-arterial injection, intra-peritoneal injection and subcutaneous injection, and
wherein the sufficient number of donor lymphocytes is between about $1\times10^3$ and about $1\times10^8$ cells; and
(2) allowing the inflammatory skin condition to develop, wherein the inflammatory skin condition develops within about 70 days following administration of the donor lymphocytes to the recipient mouse, and wherein the inflammatory skin condition exhibits at least 75 percent of the symptoms selected from the group consisting of: (1) erythematous skin with loose whitish scales; (2) acanthosis, hyperkeratosis and focal parakeratosis; (3) keratinocyte hyper proliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit the changes in cytokine expression patterns observed in the skin of human patients with psoriasis.

22. A method of preparing a mouse model of an inflammatory skin condition, comprising:

(1) administering to a recipient mouse a sufficient number of donor lymphocytes that are CD4$^+$/CD45RB$^{high}$ T cells derived from BALB/cJ donor mice or F$_2$ progeny of BALB/cJ×129/SvJ donor mice expressing the H-2$^d$ MHC haplotype, wherein the recipient mouse is selected from the group consisting of a scid mouse, an athymic mouse, an irradiated mouse, a RAG-2 deficient mouse, a CD-3 deficient mouse, a TCRαβ deficient mouse and a T cell signaling defective mouse, wherein administering the lymphocytes comprises a method selected from the group consisting of intravenous injection, retro-orbital injection, intra-arterial injection, intra-peritoneal injection and subcutaneous injection, and wherein the sufficient number of donor lymphocytes is between about 1×10$^3$ and about 1×10$^8$ cells; and (2) allowing the inflammatory skin condition to develop, wherein the inflammatory skin condition develops within about 70 days following administration of the donor lymphocytes to the recipient mouse, and wherein the inflammatory skin condition exhibits at least 75 percent of the symptoms selected from the group consisting of: (1) erythematous skin with loose whitish scales; (2) acanthosis, hyperkeratosis and focal parakeratosis; (3) keratinocyte hyper proliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis.

23. A method of preparing a mouse model of an inflammatory skin condition, comprising:

(1) administering to a recipient mouse from the C.B-17/Tac-sciDF$^{scid/scid}$ lineage a sufficient number of donor lymphocytes that are derived from donor mice expressing the H-2$^d$ MHC haplotype, wherein the donor lymphocytes are selected from the group consisting of: α$^E$ deficient splenocytes, α$^E$ deficient naive CD4$^+$ T-lymphocytes, α$^E$ deficient CD4$^+$/CD45RB$^{hi}$ T-lymphocytes, α$^E$ deficient naive CD8$^+$ T-lymphocytes, naive CD4$^+$ T-lymphocytes, naive CD8$^+$ T-lymphocytes, naive CD4$^-$/CD8$^-$ T-lymphocytes, α$^E$ deficient naive CD4$^-$/CD8$^-$ T-lymphocytes and α$^E$ wild-type CD4$^+$/CD45RB$^{hi}$ T-lymphocytes, wherein administering the lymphocytes comprises a method selected from the group consisting of intravenous injection, retro-orbital injection, intra-arterial injection, intra-peritoneal injection and subcutaneous injection, and wherein the sufficient number of donor lymphocytes is between about 1×10$^3$ and about 1×10$^8$ cells; and (2) allowing the inflammatory skin condition to develop, wherein the inflammatory skin condition develops within about 70 days following administration of the donor lymphocytes to the recipient mouse, and wherein the inflammatory skin condition exhibits at least 75 percent of the symptoms selected from the group consisting of: (1) erythematous skin with loose whitish scales; (2) acanthosis, hyperkeratosis and focal parakeratosis; (3) keratinocyte hyper proliferation; (4) changes in keratinocyte differentiation; (5) increased expression of MHC class II in one or more skin lesions; (6) increased expression of ICAM-1 in one or more skin lesions; (7) dermal angiogenesis; (8) dilation of blood vessels; (9) increased number of dermal mast cells; (10) infiltration of the dermis with neutrophils; (11) formation of microabscesses within the epidermis; and (12) changes in cytokine expression patterns that exhibit changes in cytokine expression patterns observed in the skin of human patients with psoriasis.

\* \* \* \* \*

```
                    SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
         (A) LENGTH: 25 base
pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: YES (vi) ORIGINAL SOURCE:
         (A) ORGANISM: Rattus ra
ttus (xi) SEQUENCE DESCRIPTION: SEQ ID NO:1:

CCGGAATTCA GCGCCTCGGC TTGTC
                25
```